(12) United States Patent
Kim et al.

(10) Patent No.: US 10,718,761 B2
(45) Date of Patent: Jul. 21, 2020

(54) PHOSPHATASE OR KINASE ACTIVITY DETECTION COMPOSITION AND DETECTION METHOD

(71) Applicant: INDUSTRY-UNIVERSITY COOPERATION FOUNDATION HANYANG UNIVERSITY, Seoul (KR)

(72) Inventors: Young Pil Kim, Seoul (KR); Jin Oh Lee, Seoul (KR); Gae Baik Kim, Seoul (KR); Bu Teak Lim, Seoul (KR)

(73) Assignee: INDUSTRY—UNIVERSITY COOPERATION FOUNDATION HANYANG UNIVERSITY (KR)

( * ) Notice: Subject to any disclaimer, the term of this patent is extended or adjusted under 35 U.S.C. 154(b) by 156 days.

(21) Appl. No.: 15/624,018

(22) Filed: Jun. 15, 2017

(65) Prior Publication Data

US 2017/0350881 A1 Dec. 7, 2017

Related U.S. Application Data

(63) Continuation-in-part of application No. PCT/KR2015/013849, filed on Dec. 17, 2015.

(30) Foreign Application Priority Data

Dec. 19, 2014 (KR) .................. 10-2014-0184843

(51) Int. Cl.
*G01N 33/542* (2006.01)
*C12Q 1/42* (2006.01)
*C12Q 1/48* (2006.01)
*G01N 21/64* (2006.01)

(52) U.S. Cl.
CPC ............. *G01N 33/542* (2013.01); *C12Q 1/42* (2013.01); *C12Q 1/485* (2013.01); *G01N 2021/6432* (2013.01); *G01N 2021/6441* (2013.01)

(58) Field of Classification Search
None
See application file for complete search history.

(56) References Cited

U.S. PATENT DOCUMENTS

| 6,066,462 A * | 5/2000 | Goueli | C07K 7/06 435/7.1 |
| 2003/0119072 A1 * | 6/2003 | Hoekstra | C12Q 1/25 435/7.2 |
| 2005/0245726 A1 * | 11/2005 | Lee | C07K 7/06 530/328 |
| 2009/0305254 A1 * | 12/2009 | Sode | C12Q 1/6825 435/6.11 |
| 2013/0331398 A1 * | 12/2013 | Morabito | A61K 31/00 514/254.05 |

FOREIGN PATENT DOCUMENTS

| KR | 10-0740891 | 7/2007 |
| KR | 1020140043582 | 4/2014 |

OTHER PUBLICATIONS

Lim, B et al. Zn(II)-coordinated quantum dot-FRET nanosensors for the detection of protein kinase activity. Sensors. 2015. 15: 17977-17989. Published Jul. 23, 2015. (Year: 2015).*
Shiosaki, S et al. A protein kinase assay based on FRET between quantum dots and fluorescently-labeled peptides. Chem. Commun. 2013. 49: 5592-5594. Published Apr. 30, 2013. (Year: 2013).*
Manzerra, P et al. Zinc induces a Src family kinase-mediated up-regulation of NMDA receptor activity and excitotoxicity. PNAS. 2001. 98(20): 11055-11061. (Year: 2001).*
Li, Y et al. Fluorescence detection techniques for protein kinase assay. Analytical and Bioanalytical Chemistry. 2008. 390(8): 2049-2057. (Year: 2008).*
Tanaka, T et al. Quantitative analysis of lysophosphatidic acid by time-of-flight mass spectrometry using a phosphate-capture molecule. Journal of Lipid Research. 2004. 45: 2145-2150. (Year: 2004).*
International Search Report for PCT/KR2015/013849, dated Mar. 31, 2016, 2 pages.
Lee et al., "Rapid Detection of Protein Phosphatase Activity Using Zn(II)-Coordinated Gold Nanosensors Based on His-Tagged Phosphopeptides", Anal. Chem, 2015, 87, 1257-1265.
Ni et al., "Analyzing protein kinase dynamics in living cells with FRET reporters", Methods 40 (2006) 279-286.
Rodems et al., "A FRET-Based Assay Platform for Ultra-High Density Drug Screening of Protein Kinases and Phosphatases", ASSAY and Drug Development Technologies, vol. 1, No. 1-1, 2002.

* cited by examiner

*Primary Examiner* — Susan E. Fernandez
(74) *Attorney, Agent, or Firm* — Adsero IP

(57) ABSTRACT

The present invention relates to a composition for detecting phosphatase or kinase activity and a method of detecting phosphatase or kinase activity. The kinase or phosphatase activity may be quantitatively measured in real time by using the composition of the present invention.

5 Claims, 20 Drawing Sheets

PHOSPHATASE OR KINASE ACTIVITY DETECTION COMPOSITION AND DETECTION METHOD

CROSS-REFERENCE TO RELATED APPLICATION

This application claims priority to and is a Continuation-In-Part of PCT/KR2015/013849 (WO2016/099167), filed on Dec. 17, 2015 entitled "PHOSPHATASE OR KINASE ACTIVITY DETECTION COMPOSITION AND DETECTION METHOD", which application claims priority to and the benefit of Korean Patent Application No. 10-2014-0184843, filed on Dec. 19, 2014, the disclosures of which are incorporated herein by reference in their entirety. Any disclaimer that may have occurred during the prosecution of the above-referenced applications is hereby expressly rescinded, and reconsideration of all relevant art is respectfully requested.

BACKGROUND

1. Field of Invention

The present invention is supported by Researcher Program (project No. 2013R1A2A2A03015161) through the National Research Foundation funded by the Minister of Science, ICT and Future Planning of the Republic of Korea. The research project is titled "Study on Expression and Activity of Disease Biomarkers Based on SNWE Analysis using DNAzymes and Nanosensors. The research institute is the Industry-Academic Cooperation Foundation of Hanyang University, and the research period is from Jun. 1, 2013 to May 31, 2016.

In addition, the present invention is supported by Nano-Material Technology Development Program (project No. 2012M3A7B4035286) through the National Research Foundation funded by the Minister of Science, ICT and Future Planning of the Republic of Korea. The research project is titled "Development of Integrated Sensor Systems for Early Stage Detection of Disease Biomarkers Based on Composite Nanostructures". The research institute is the Industry-Academic Cooperation Foundation of Hanyang University, and the research period is from Jun. 30, 2012 to Jun. 29, 2017.

The present invention relates to a composition for detecting phosphatase or kinase activity and a method of detecting phosphatase or kinase activity.

2. Discussion of Related Art

To detect phosphatase or kinase activity, the following conventional methods have been used.

A method using a phosphopeptide-specific antibody is a method of indirectly analyzing the amount of phosphate groups by distinguishing only peptides phosphorylated by a kinase by using an antibody specifically binding to phosphate groups, binding a peroxidase-conjugated secondary antibody to the phosphate group-conjugated antibody, and then measuring a signal generated while the substrate is decomposed by a peroxidase (Promega, ADP-Glo™ Kinase Assay). According to this method, expensive antibodies are used, the measurement time is long, and the measurement method relies on phosphorylated signals. Thus, when this method is used for dephosphorylation measurement, the method relies on a decreased signal rather than an increased signal, and thus has a limitation in quantitative analysis.

Measurement using phosphatase fluorescence and a phosphopeptide substrate is a method wherein an antibody for specifically binding to a phosphatase is immobilized in each well of a plate, followed by binding of the phosphatase thereto, and then, when dephosphorylation occurs, a substrate exhibiting a fluorescence signal by the dissociated phosphate group is treated to thereby measure phosphatase activity. This method is advantageous in that kinetic data for enzymatic activity is rapidly acquired, but is disadvantageous in that there are relatively high background signal values in mixed sample analysis and a need for additional equipment for fluorescence analysis (R&D, Malachite Green Phosphate Detection Kit).

In a method of analyzing protease activity using agglomeration of gold nanoparticles (Korean Patent Application Publication No. 10-2014-0043582), the agglomeration of gold nanoparticles is realized through peptides, metal ions, and the like, but metal ions have no specificity to phosphorylation, and thus it is difficult to apply this method to phosphorylation-related enzymes.

Therefore, there is a need to develop a technology of effectively detecting phosphatase activity without the problems of the prior art.

Throughout the present specification, many papers and patent documents are referred to and citations thereof are shown. The disclosures of the cited papers and patent documents are incorporated herein by reference in their entirety, and thus the level of the art to which the present invention pertains and the contents of the present invention will be explained more clearly.

SUMMARY OF THE INVENTION

The inventors of the present invention intensively studied and tried to develop a method of real-time and quantitatively measuring kinase or phosphatase activity. As a result, they verified that, when zinc ions, a zinc ion receptor comprising a chelating ligand, and a kinase or phosphatase peptide substrate are used, kinase or phosphatase activity can be quantitatively measured in real time, thus completing the present invention.

Thus, an object of the present invention is to provide a composition for measuring kinase or phosphatase activity.

Another object of the present invention is to provide a method of measuring kinase or phosphatase activity.

Other objects and advantages of the present invention become more apparent by the detailed description, claims, and drawings of the invention.

DETAILED DESCRIPTION OF THE INVENTION

According to an aspect of the present invention, there is provided a composition for measuring kinase or phosphatase activity, the composition including (a) zinc ions ($Zn^{2+}$), (b) a zinc ion receptor comprising a chelating ligand, and (c) a kinase or phosphatase peptide substrate, and exhibiting a phosphorylation or dephosphorylation detection signal according to a change in the phosphorylation state of a peptide substrate.

The inventors of the present invention intensively studied and tried to develop a method of real-time and quantitatively measuring kinase or phosphatase activity. As a result, they verified that, when zinc ions, laia zinc ion receptor comprising a chelating ligand, and a kinase or phosphatase peptide substrate are used, kinase or phosphatase activity can be quantitatively measured in real time.

In the present invention, the type of kinase or phosphatase used for activity measurement is not limited, and a kinase or phosphatase may be used together with a suitable peptide substrate including a target peptide sequence capable of inducing phosphorylation or dephosphorylation by the corresponding enzyme. For example, the kinase or phosphatase includes: the protein tyrosine phosphatase family including receptor tyrosine phosphates, non-receptor tyrosine phosphatases, low-molecular-weight phosphotyrosine protein phosphatases, Cdc25 phosphatases, and the like; and the serine/threonine phosphatase family including protein phosphatase 1 (PP1), protein phosphatase 2 (PP2A), calcineurin (PP3), PP4, PP5, PP6, and the like.

The peptide substrate of the present invention may be a peptide having an amino acid sequence having specific phosphorylation activity for a kinase in the measurement of phosphorylation activity of the kinase, and a known peptide substrate according to the type of kinase may be used. In the measurement of dephosphorylation activity of a phosphatase, the amino acid sequence of the peptide substrate is not particularly limited. In the case of the above-described PTP family, a phosphorylated serine/threonine-containing peptide may be used for phosphorylated tyrosine, and serine/threonine phosphatase families For example, a phosphorylated tyrosine-containing oligopeptide may be used for T-cell protein tyrosine phosphatase (TC PTP), a phosphorylated tyrosine/serine/threonine may be used for lambda protein phosphatase (Lambda PP), and a phosphorylated serine/threonine-containing oligopeptide may be used for protein phosphatase 1 (PP1). The oligopeptide used as a peptide substrate in the present invention includes 4 to 30 amino acids, in particular, 4 to 25 amino acids, more particularly, 4 to 20 amino acids, even more particularly, 4 to 15 amino acids, most particularly, 4 to 12 amino acids. The oligopeptide includes one or more phosphorylated serine, threonine, and/or tyrosine as described above to measure phosphatase activity, and may be determined according to the type of phosphatase.

According to the present invention, the kinase or phosphatase activity is measured by detecting a detection signal generated by the interaction between zinc ions ($Zn^{2+}$) and the zinc ion receptor and the phosphorylated peptide substrate. The term "zinc ion receptor including a chelating ligand" as used herein refers to a receptor that chelates a metal ion, in particular, zinc ions ($Zn^{2+}$), and any chelating ligand may be used without particular limitation as long as it is a functional group capable of forming a chelating bond by electrostatic attraction with zinc ions, which are divalent cations. The zinc ion receptor may immobilize zinc ions on a surface thereof by electrostatic attraction between a carboxylic group present on a surface thereof and the zinc ions.

The zinc ions of the present invention may be provided in the form of $Zn^{2+}$, and, in particular, may be provided by a compound such as $ZnCl_2$ or $ZnSO_4$, but the present invention is not limited thereto.

In one embodiment of the present invention, the peptide substrate of the present invention includes any one selected from (a) a fluorescence signal-generating donor fluorophore and (b) a fluorophore acceptor that quenches the fluorescence signal by causing fluorescence resonance energy transfer (FRET) with the donor fluorophore, and the zinc ion receptor includes any other except for a donor fluorophore and a fluorophore acceptor. The composition for measuring kinase or phosphatase activity of the present invention measures enzymatic activity by detecting a detection signal generated by the interaction between zinc ions ($Zn^{2+}$) and the zinc ion receptor and the phosphorylated peptide substrate. The phosphorylated peptide substrate forms a bond with zinc ions by electrostatic attraction. The term "bond" formed by electrostatic attraction between the phosphorylated peptide substrate and zinc ions refers to an ion-ion bond, and such interaction allows the peptide substrate, zinc ions, and the zinc ion receptor to maintain interatomic or intermolecular spacing therebetween by a bond distance. A dephosphorylated peptide substrate does not form a bond with zinc ions, and thus has a relatively long distance therefrom. At this time, a phosphorylated peptide substrate may be distinguished from a dephosphorylated peptide substrate by using a FRET phenomenon, and, furthermore, the degree of phosphorylation thereof may be detected. For this, the peptide substrate may include one of a donor fluorophore and a fluorophore acceptor that causes the FRET phenomenon for the peptide substrate and the zinc ion receptor.

The term "fluorescence resonance energy transfer" as used herein refers to a phenomenon where two types of fluorescent materials in close proximity transfer energy by resonance. When an energy transferring donor emits a photon by dropping from an excited state to a ground state, an acceptor receives it when the two fluorescent molecules are in close proximity, thereby emitting light with a different wavelength. The intensity of light emitted by FRET is related to a distance between two molecules, and thus a distance between two fluorescent materials may be identified by FRET.

The term "donor fluorophore" as used herein refers to a fluorescence signal donor that transfers energy among two substances that cause the FRET phenomenon. The wavelength of a fluorescence signal provided by the donor fluorophore varies, and is generally in the range of 500 nm to 700 nm.

The term "fluorescence signal" used when defining the term "donor fluorophore" refers to light emitted by a specific material defined as the donor fluorophore.

The donor fluorophore of the present invention may be any donor fluorophore known in the art, examples of the donor fluorophore include (the number in parentheses denotes a maximum emission wavelength expressed in units of nanometers):

FITC (518), Cy2™ (506), YO-PRO™-1 (509), YOYO™-1 (509), Calcein (517), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Di1 (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red(615), Nile Red (628), YO-PRO™-3 (631), YOYO™-3 (631), R-phycocyanin (642), C-Phycocyanin (648), TO-PRO™-3 (660), TOTO3 (660), DiD Di1C(5) (665), CyS™ (670), Thiadicarbocyanine (671), and Cy5.5 (694).

The term "acceptor" as used herein refers to a substance that serves to quench a fluorescence signal emitted from the donor fluorophore. Any acceptor known in the art that causes FRET with the donor fluorophore may be used.

Suitable donor fluorophore-acceptor pairs are disclosed in the various following documents: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; and U.S. Pat. Nos. 3,996,345 and 4,351,760.

In one embodiment of the present invention, TAMRA is used as the donor fluorophore, and quantum dot (QD) 525 is used as the acceptor, but the present invention is not limited thereto.

In particular, the peptide substrate of the present invention may include, for example, a donor fluorophore linked to one terminal of a peptide by a chemical bond, and zinc ions may bind to a surface of the fluorophore acceptor of the present invention. In another embodiment, the fluorophore acceptor may bind to one terminal of the peptide substrate of the present invention, and the donor fluorophore may be surface-modified so as to bind to zinc ions.

In one embodiment of the present invention, the peptide substrate of the present invention may be immobilized on a support. The support on which the peptide substrate of the present invention can be immobilized may be any support known in the art without particular limitation, and non-limiting examples of the support include a gel-type support, a polymer support, a bead-type support such as agarose beads, a plate support such as a well plate, a glass substrate, and a metal substrate. The kinase or phosphatase activity may be measured by adding zinc ions and a zinc ion receptor including a donor fluorophore in a state in which a peptide substrate is immobilized on a support, and bringing the resultant in contact with a kinase or phosphatase.

In one embodiment of the present invention, the peptide substrate of the present invention may further include biotin, and the support of the present invention may be NeutrAvidin agarose beads. The biotin of the present invention may be included in the peptide substrate in the form of being bound to one terminal of the peptide substrate, and may be immobilized on NeutrAvidin agarose beads through the interaction therewith. The term "NeutrAvidin agarose beads" as used herein refers to beads coated with NeutrAvidin agarose, and, when a peptide substrate attached to the beads is used, the FRET phenomenon occurring between a donor fluorophore bound to the peptide substrate and an additionally added fluorophore acceptor may be detected more efficiently.

In one embodiment of the present invention, the peptide substrate of the present invention includes a polyhistidine, and the zinc ion receptor including a chelating ligand may be metal nanoparticles that are surface-modified with a chelating ligand. In particular, the polyhistidine of the present invention may be bound to one terminal of the peptide substrate via a peptide bond, and the zinc ion receptor including a chelating ligand of the present invention may be chelating ligand-containing metal nanoparticles. The term "metal nanoparticles" as used herein refers to metal particles having a particle size of several nanometers to tens of nanometers, and metal nanoparticles that are surface-modified with a chelating ligand-containing compound may be used. The kinase or phosphatase activity may be quantitatively analyzed as a relative ratio using two or more absorption peaks according to the characteristics of nanoparticles. In addition, time-based kinetic analysis of a kinase or phosphatase is possible.

In one embodiment of the present invention, the metal nanoparticles of the present invention include any one selected from the group consisting of gold, silver, copper, platinum, palladium, nickel, and iron, or a mixture of two or more thereof.

In one embodiment of the present invention, the metal nanoparticles of the present invention may have an average diameter ranging from 2 nm to 50 nm, preferably, from 3 nm to 30 nm. Optical properties such as absorbance may vary by self-assembly of metal nanoparticles within the above-described average diameter. The self-assembly of metal nanoparticles may be quantitatively detected by measuring an absorbance ratio of two wavelengths exhibiting absorbance changes.

As the frequency of the self-assembly of metal nanoparticles increases, a wavelength exhibiting maximum absorbance is red-shifted, and the maximum absorbance value also decreases. In addition, the self-assembly of metal nanoparticles may be quantitatively detected using various known methods.

In one embodiment of the present invention, the metal nanoparticles of the present invention may be surface-modified with one or more selected from the group consisting of nitrilotriacetic acid (NTA), ethylene diamine tetraacetic acid (EDTA), ethylene glycol tetraacetic acid (EGTA), diethylene triamine pentaacetic acid (DTPA), phenanthroline (PHEN), N,N,N',N'-tetrakis(2-pyridylmethyl)ethylenediamine (TPEN), N-(2-hydroxyethyl)ethylenediamine-N,N',N'-triacetic acid (HEDTA), and 1,3-bis[bis(pyridin-2-ylmethyl)amino]propan-2-olato (Phos-tag).

In one embodiment of the present invention, the polyhistidine of the present invention consists of 4 to 10 histidines. For example, a generally used polyhistidine consisting of at least six histidines may be used. The inventors of the present invention verified that, when the self-assembly of metal nanoparticles is used to measure kinase or phosphatase activity, self-assembly occurs only in a case in which a polyhistidine is included at one terminal of the peptide substrate, and self-assembly does not occur even though the peptide substrate is in a phosphorylated form in a case in which the peptide substrate does not include a polyhistidine.

The peptide substrate of the present invention may be referred to the foregoing detailed description. In a particular embodiment of the present invention, to measure phosphatase activity using agglomeration of nanoparticles, GLR-RAS$_{(p)}$LG(pep3), which is a phosphorylated form of a peptide sequence of GLRRASLG, H$_6$GLRRASLG(pep2), which is a histidine-tagged form, and H$_6$GLRRAS$_{(p)}$LG (pep1), which is a phosphorylated and histidine-tagged form, are used. At this time, a phosphatase has no sequence specificity for the oligopeptides used in the embodiments and an amino acid sequence thereof may be appropriately varied. In another embodiment of the present invention, KEEPPSPPQSPR, KEEPPSPPQS$_{(p)}$PR, and KEEPPS$_{(p)}$PQS$_{(p)}$PR are used, but the present invention is not limited thereto.

According to another aspect of the present invention, there is provided a method of measuring phosphatase activity, including the following processes:

(i) preparing a composition for measuring phosphatase activity, in which the composition includes (a) zinc ions, (b) a fluorophore acceptor as a zinc ion receptor comprising a chelating ligand, and (c) a phosphorylated phosphatase peptide substrate to which a donor fluorophore is bound, and a fluorescence signal of the donor fluorophore is quenched by the interaction between the zinc ions and the fluorophore acceptor; and (ii) detecting the recovery of the fluorescence signal having been quenched by FRET by contacting the composition for measuring phosphatase activity with a phosphatase.

In the method of measuring phosphatase activity of the present invention, the detecting of the recovery of the fluorescence signal may be performed using any fluorescence signal detection method known in the art without limitation.

The composition for measuring phosphatase activity, used in the method of measuring phosphatase activity, has already been described, and thus a detailed description thereof will be omitted to avoid excessive complexity of the description of the present specification.

According to another aspect of the present invention, there is provided a method of measuring kinase activity, including the following processes:

(i) preparing a composition for measuring kinase activity, in which the composition includes: (a) zinc ions; (b) a fluorophore acceptor as a zinc ion receptor comprising a chelating ligand, and (c) a kinase peptide substrate to which a donor fluorophore is bound, and the kinase peptide substrate includes one or more dephosphorylated phosphorylation site peptides; and (ii) detecting the quenching of a fluorescence signal by FRET by contacting the composition for measuring kinase activity with a kinase.

In the method of measuring kinase activity, the detecting of the quenching may be performed by measuring a fluorescence signal decrease using a generally known fluorescence signal detection method, but the fluorescence signal detection method is not particularly limited.

The composition for measuring kinase activity, used in the method of measuring kinase activity, has already been described, and thus a detailed description thereof will be omitted to avoid excessive complexity of the description of the present specification.

According to another aspect of the present invention, there is provided a method of measuring phosphatase activity, including the following processes:

(i) preparing a composition for measuring phosphatase activity, in which the composition includes: (a) zinc ions; (b) metal nanoparticles that are surface-modified so as to have a chelating ligand; and (c) a phosphorylated phosphatase peptide substrate including a polyhistidine, and the zinc ions, the metal nanoparticles, and the peptide substrate are self-assembled by interactions therebetween; and (ii) detecting the disassembly of the self-assembled structure of the composition by contacting the composition for measuring phosphatase activity with a phosphatase.

In one embodiment of the present invention, the metal nanoparticles include any one selected from the group consisting of gold, silver, copper, platinum, palladium, nickel, and iron or a mixture of at least two thereof.

The composition for measuring phosphatase activity, used in the method of measuring phosphatase activity, has already been described, and thus a detailed description thereof will be omitted to avoid excessive complexity of the description of the present specification.

According to another aspect of the present invention, there is provided a method of measuring kinase activity, including the following processes:

(i) preparing a composition for measuring kinase activity, in which the composition includes: (a) zinc ions; (b) metal nanoparticles that are surface-modified so as to have a chelating ligand; and (c) a kinase peptide substrate including a polyhistidine, and the kinase peptide substrate includes one or more dephosphorylated phosphorylation site peptides; and (ii) detecting an increase in the self-assembled structure of the composition by contacting the composition for measuring kinase activity with a kinase.

In one embodiment of the present invention, the metal nanoparticles include any one selected from the group consisting of gold, silver, copper, platinum, palladium, nickel, and iron or a mixture of at least two thereof.

The composition for measuring kinase activity, used in the method of measuring kinase activity, has already been described, and thus a detailed description thereof will be omitted to avoid excessive complexity of the description of the present specification.

According to another aspect of the present invention, there is provided a method of screening a phosphatase activity inhibitor, including the following processes:

(i) preparing a composition for measuring phosphatase activity, in which the composition includes: (a) zinc ions; (b) metal nanoparticles that are surface-modified so as to have a chelating ligand; and (c) a phosphorylated phosphatase peptide substrate including a polyhistidine, and the zinc ions, the metal nanoparticles, and the peptide substrate are self-assembled by interactions therebetween; and (ii) simultaneously contacting the composition, a phosphatase inhibiting candidate, and a phosphatase, and analyzing whether or not phosphatase activity is decreased, in which, when the phosphatase activity is decreased by comparing with a control not treated with a candidate, the candidate is determined as a phosphatase inhibiting material.

The composition for measuring phosphatase activity, used in the method of screening a phosphatase activity inhibitor, has already been described, and thus a detailed description thereof will be omitted to avoid excessive complexity of the description of the present specification.

EXAMPLES

Hereinafter, the present invention will be described in further detail with reference to the following examples. It will be obvious to those of ordinary skill in the art that these examples are provided only for illustrative purposes, and are not intended to limit the scope of the present invention according to the essence of the present invention.

Example 1: Characterization of Gold Nanoparticles

Figure 3:
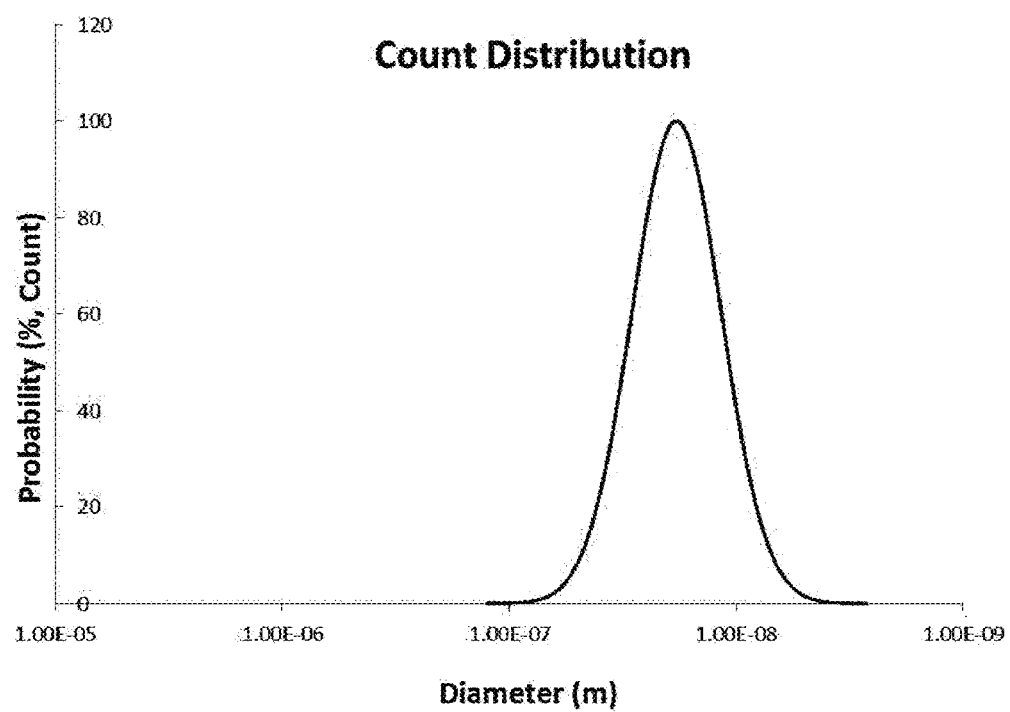
FIG. 3 illustrates measurement results of the size of gold nanoparticles surface-modified with NTA through light scattering.

Gold nanoparticles reduced using citrate were modified with polyethylene glycol having a thiol group and a carboxyl group linked to opposite ends thereof, and an amine group-linked nitrilotriactic acid (NTA) was bound thereto through a 1-ethyl-3-(3-dimethylaminopropyl)carbodiimide (EDC) reaction. The size of the gold nanoparticles surface-modified with NTA was measured by light scattering. As a result of measurement, it was confirmed that the gold nanoparticles had an average size of about 21.3 nm (see FIG. 3).

Figure 4:
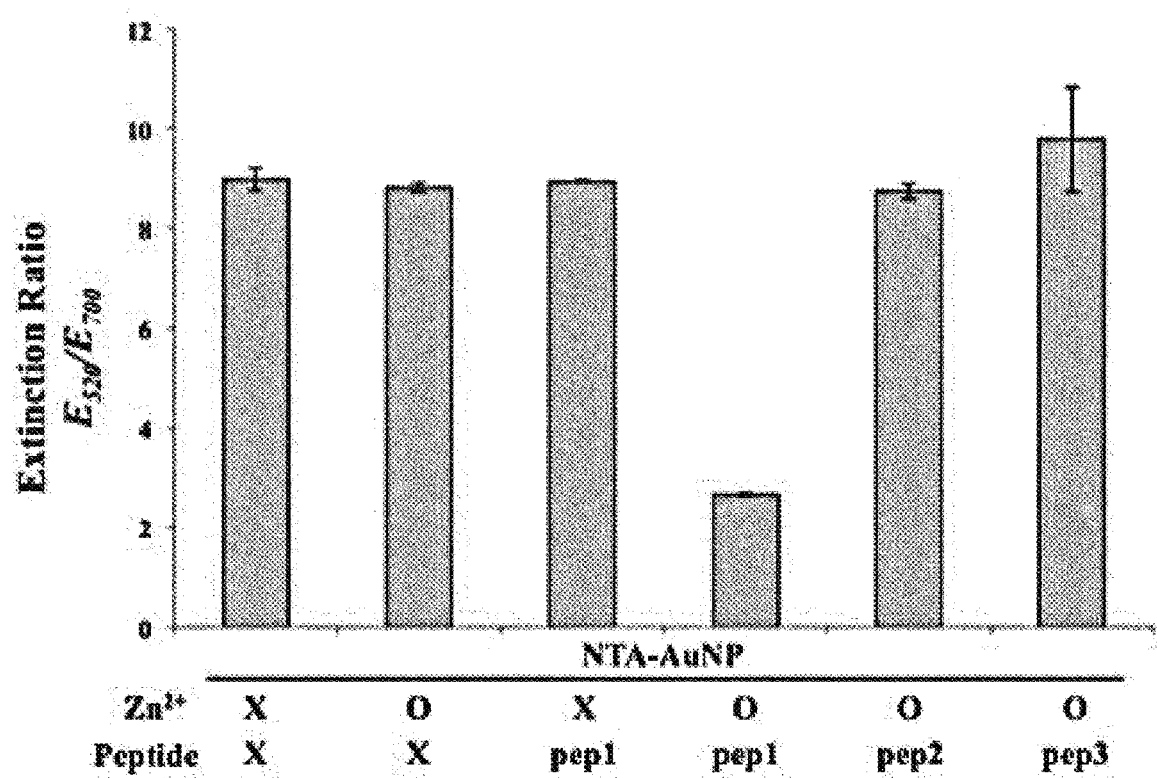
FIG. 4 illustrates test results of the self-assembly of metal nanoparticles for a peptide including a polyhistidine and/or a phosphate group or excluding any one thereof.

Example 2: $Zn^{2+}$- and Phosphopeptide-Dependent Self-Assembly of Gold Nanoparticles 5 nM gold nanoparticles, 1 mM zinc ions, and 2.5 µM peptide with a histidine tag and a phosphate group were allowed to react in Tris-HCl (pH 7.4) buffer for 1 hour, and then absorbance was measured at 520 nm and 700 nm. After measurement, an absorbance ratio of the two wavelengths was calculated, and, as a result of calculation, it was confirmed that gold nanoparticles were agglomerated specifically with respect to only a peptide having both a histidine tag and a phosphate group (see FIG. 4). In FIG. 4, pep1 denotes $H_6GLRRAS_{(p)}LG$, pep2 denotes $H_6GLRRASLG$, and pep3 denotes $GLRRAS_{(p)}LG$.

Figure 5:
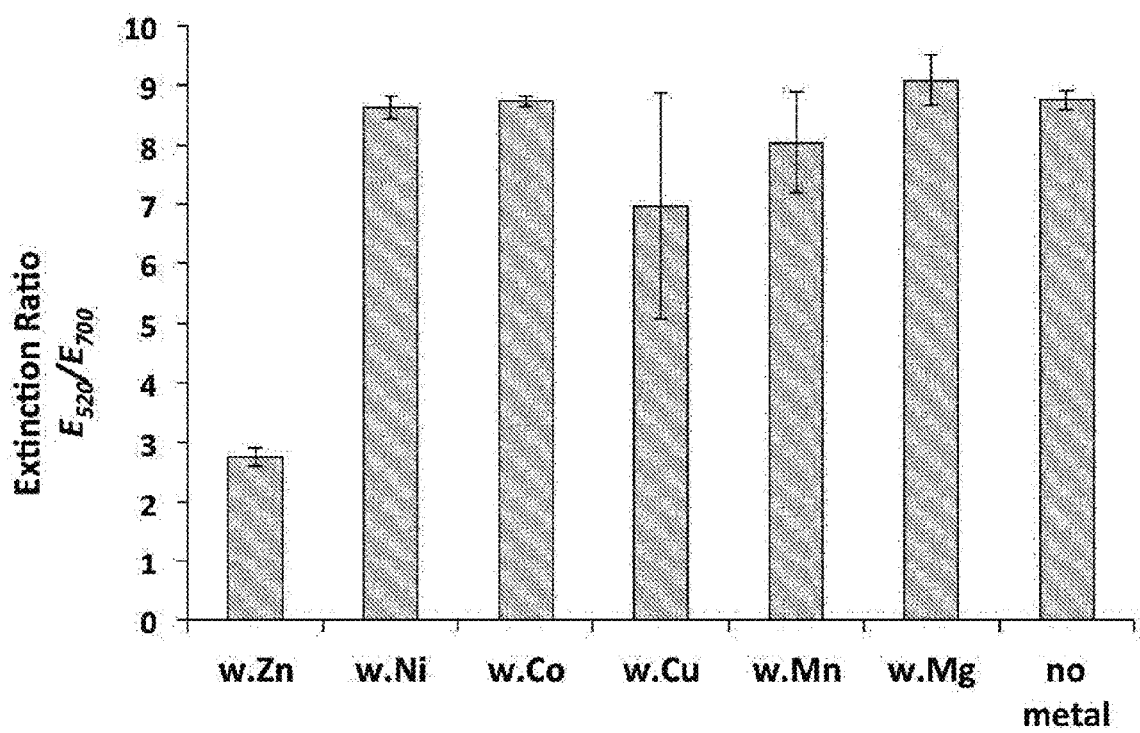
FIG. 5 illustrates test results of the self-assembly of metal nanoparticles for various types of metal ions.

Example 3: $Zn^{2+}$-Specific Self-Assembly 2.5 µM phosphopeptide, 5 nM gold nanoparticles, and various types of metal ions were allowed to react in Tris-HCl buffer (pH 7.4) for 1 hour, and then a ratio of absorbance at 520 nm to absorbance at 700 nm was obtained. As a result, it was confirmed that gold nanoparticles were agglomerated specifically only when reacted with zinc ions (see FIG. 5).

Example 4: Effect of Peptide Concentration

Figure 6:
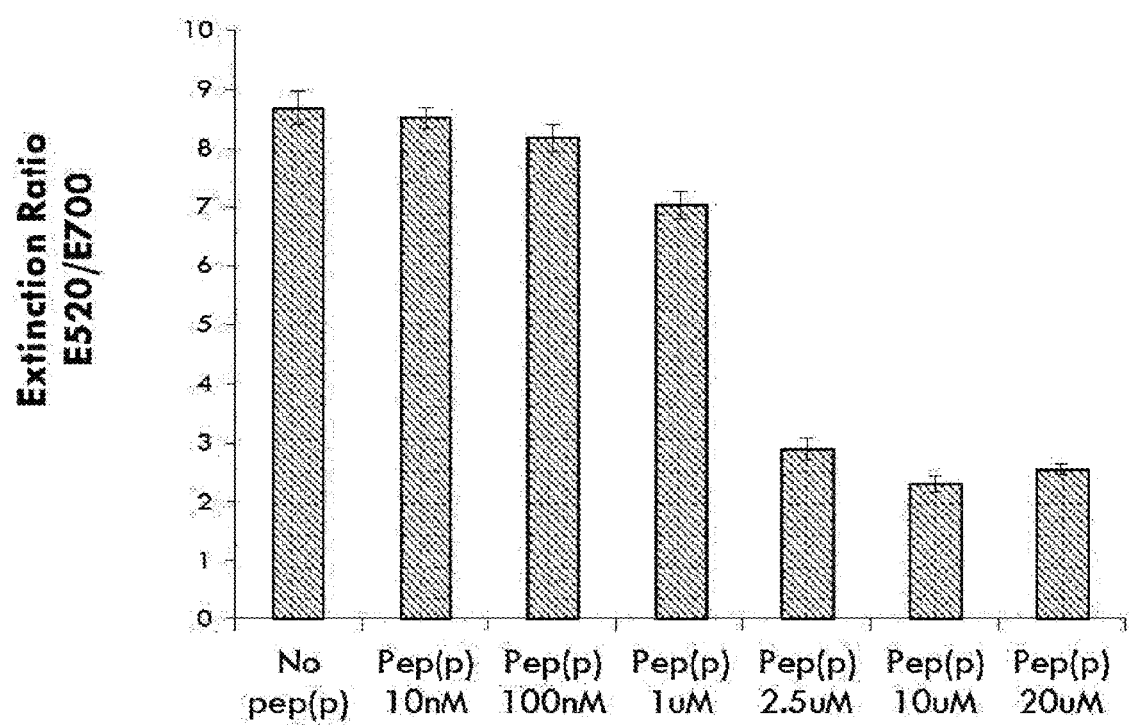
FIG. 6 illustrates test results of the self-assembly of metal nanoparticles according to peptide substrate concentration.

After a reaction between 5 µM gold nanoparticles, 1 mM zinc ions, and various concentrations of a phosphopeptide, absorbance at 520 nm/700 nm was measured. After measurement, an absorbance ratio of the two wavelengths was obtained, from which it was confirmed that saturation occurred at a phosphopeptide concentration of about 2.5 µM (see FIG. 6).

Figure 7:
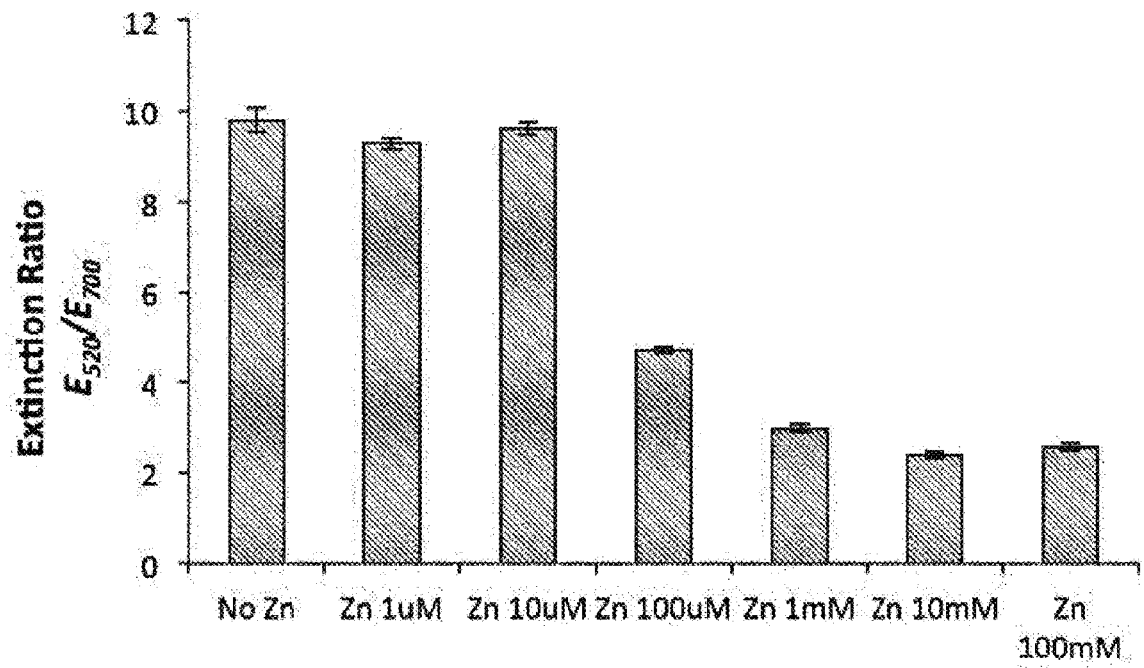
FIG. 7 illustrates test results of the self-assembly of metal nanoparticles according to zinc ion concentration.

Example 6: Effect of Zinc Concentration 5 nM gold nanoparticles, 2.5 µM phosphopeptide, and zinc ions having a concentration of 1 µM to 100 mM were allowed to react in Tris-HCl buffer (pH 7.4) for 1 hour, and absorbance at 520 nm/700 nm was measured. After measurement, an absorbance ratio of the two wavelengths was obtained, from which it was confirmed that saturation occurred at a zinc ion concentration of 1 mM (see FIG. 7).

Example 6: Phosphatase Analysis

Figure 8:
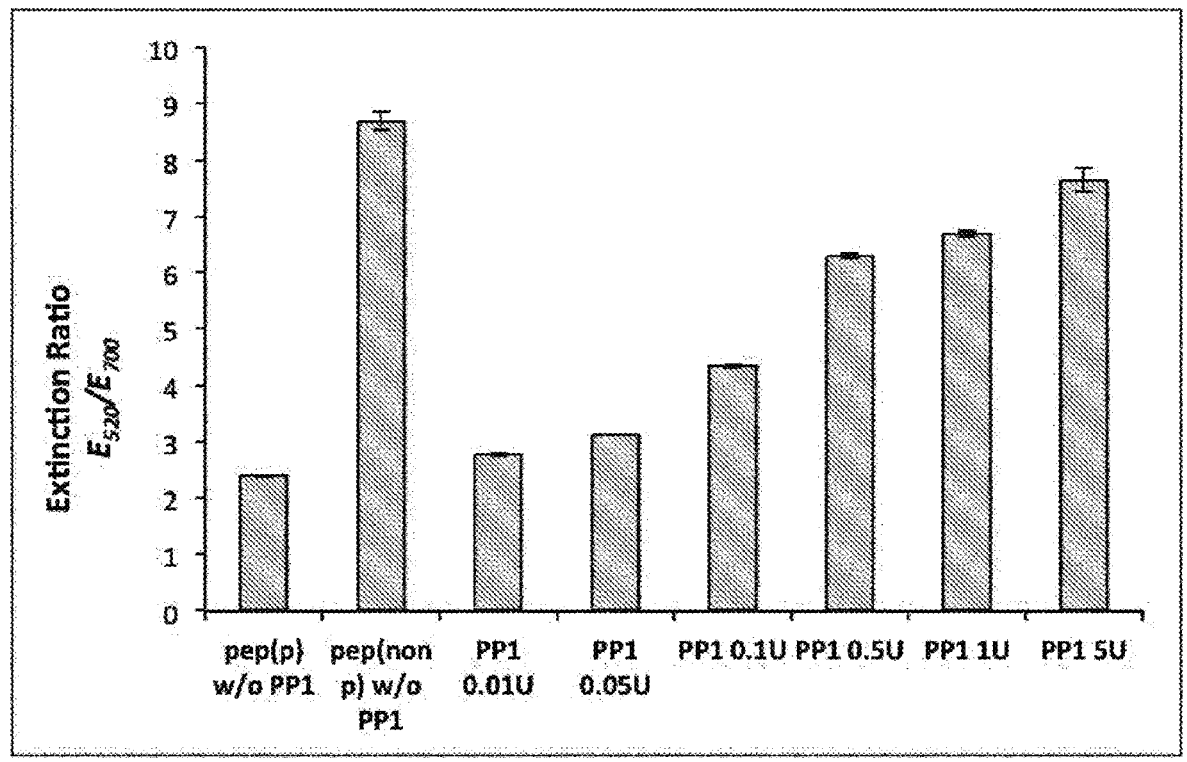
FIG. 8 illustrates test results of an absorbance ratio (520 nm/700 nm) according to treatment concentration of a phosphatase.

Various concentrations of a phosphatase, 2.5 µM phosphopeptide, and 1 mM manganese ions were allowed to react for 1 hour, and then 5 nM gold nanoparticles and 1 mM zinc ions were added thereto, and then allowed to react for 1 hour. As a result, it was confirmed that an absorbance ratio of 520 nm/700 nm was gradually recovered in proportion to the concentration of phosphatase (see FIG. 8).

Example 7: Colorimetric Assay Using Gold Nanoparticles and $Zn^{2+}$ Ions (1)

Figure 9A:
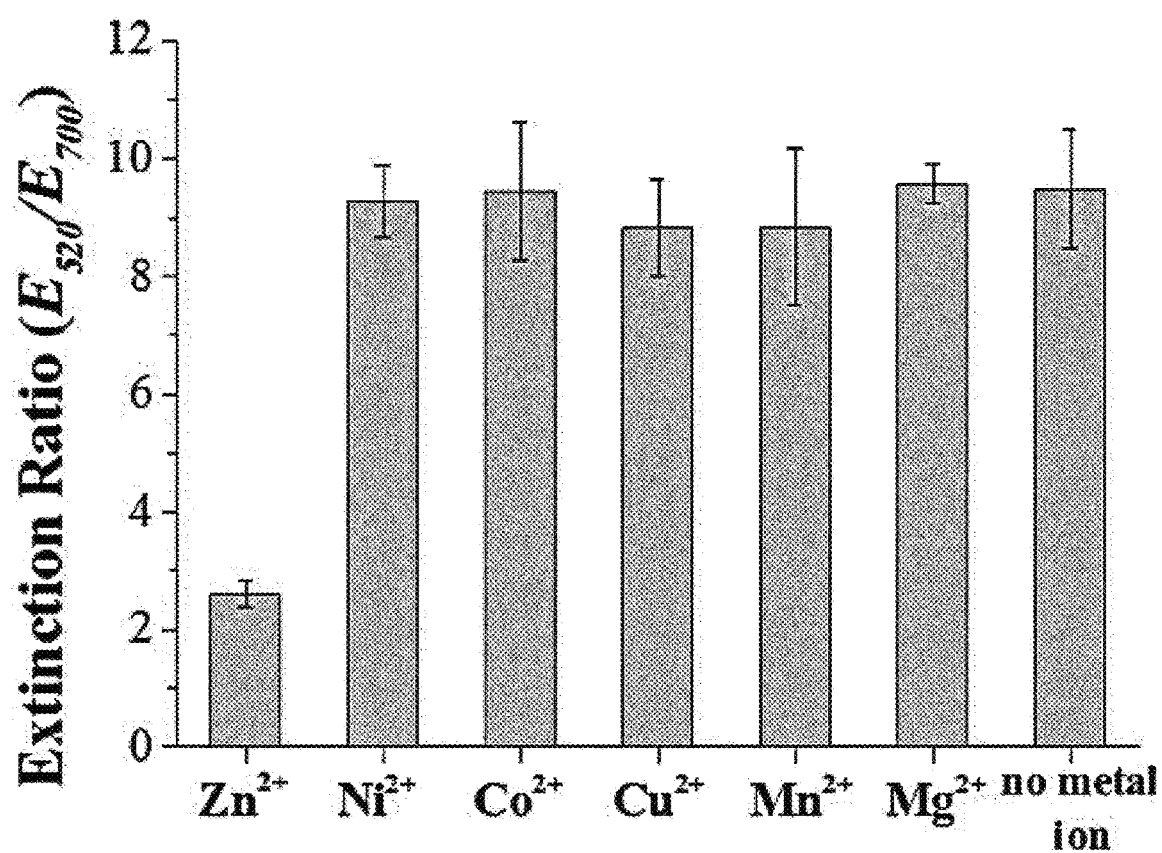
FIG. 9A illustrates colorimetric assay results of a self-assembly test of metal nanoparticles according to the type of metal ion solution.
Figure 9A:
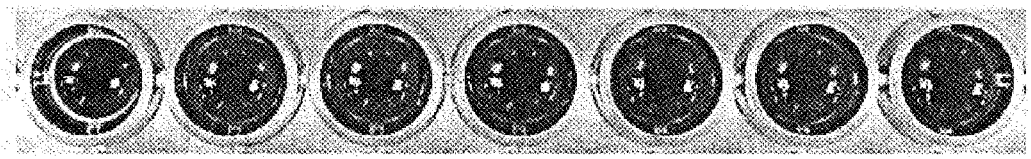

2.5 μl of gold nanoparticles surface-modified with NTA, 85 μl of 20 mM Tris buffer (pH 7.4), 10 μl of each of various types of metal ion solutions (10 mM), and 2.5 μl of 100 μM phosphopeptide were mixed in this order in a 96-well plate, and then the mixture was allowed to react at room temperature for about 1 hour, and then absorbance thereof was measured (see FIG. 9A).

Figure 9B:
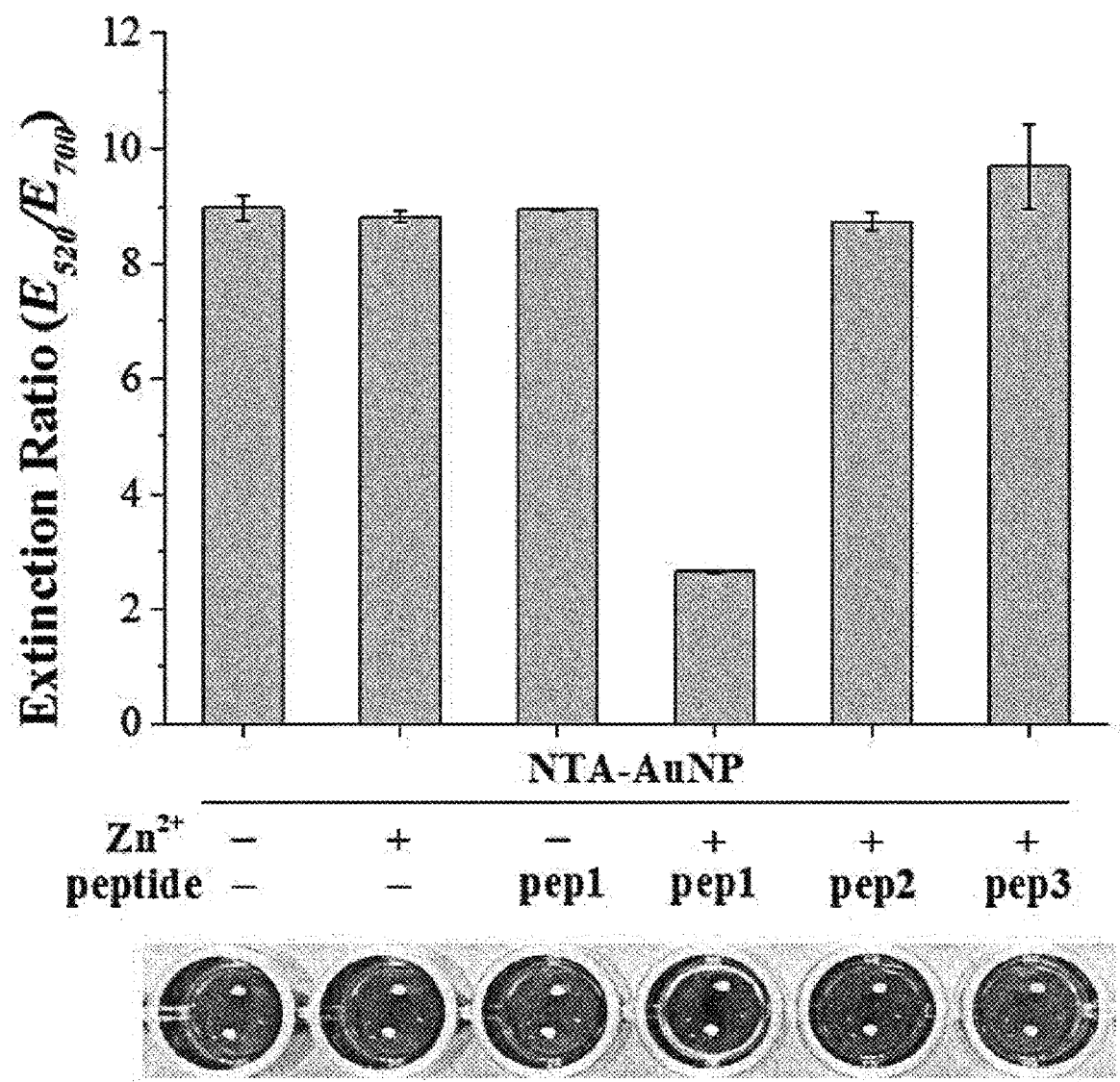
FIG. 9B illustrates colorimetric assay results of a self-assembly test of metal nanoparticles for a peptide including a polyhistidine and/or a phosphate group or excluding any one thereof.

2.5 μl of gold nanoparticles surface-modified with NTA, 85 μl of 20 mM Tris buffer (pH 7.4), 10 μl of a zinc ion solution (10 mM), and 2.5 μl of each of various types of peptides (100 μM) were mixed in this order in a 96-well plate, and then the mixture was allowed to react at room temperature for about 1 hour, and then absorbance thereof was measured (see FIG. 9B).

The experimental results were shown as a graph representing a value obtained by dividing an absorbance at 520 nm by an absorbance at 700 nm.

As a result, changes in the absorbance ratio due to self-assembly were observed only when $Zn^{2+}$ was used and when pep1 was used.

Example 8: Colorimetric Assay Using Gold Nanoparticles and $Zn^{2+}$ Ions (2)

37.5 μl of 20 mM Tris buffer, 5 μl of a manganese ion solution (10 mM), 2.5 μl of peptide (100 μM), and 5 μl of PP1 according to each concentration were mixed and then allowed to react at 30□ for 1 hour. The reaction product was added to a 96-well plate in which 37.5 μl of 20 mM Tris buffer, 2.5 μl of gold nanoparticles, and 10 μl of a $Zn^{2+}$ solution (10 mM) had been previously mixed, and then allowed to react at room temperature for 1 hour, and, thereafter, absorbance was measured.

Figure 10:
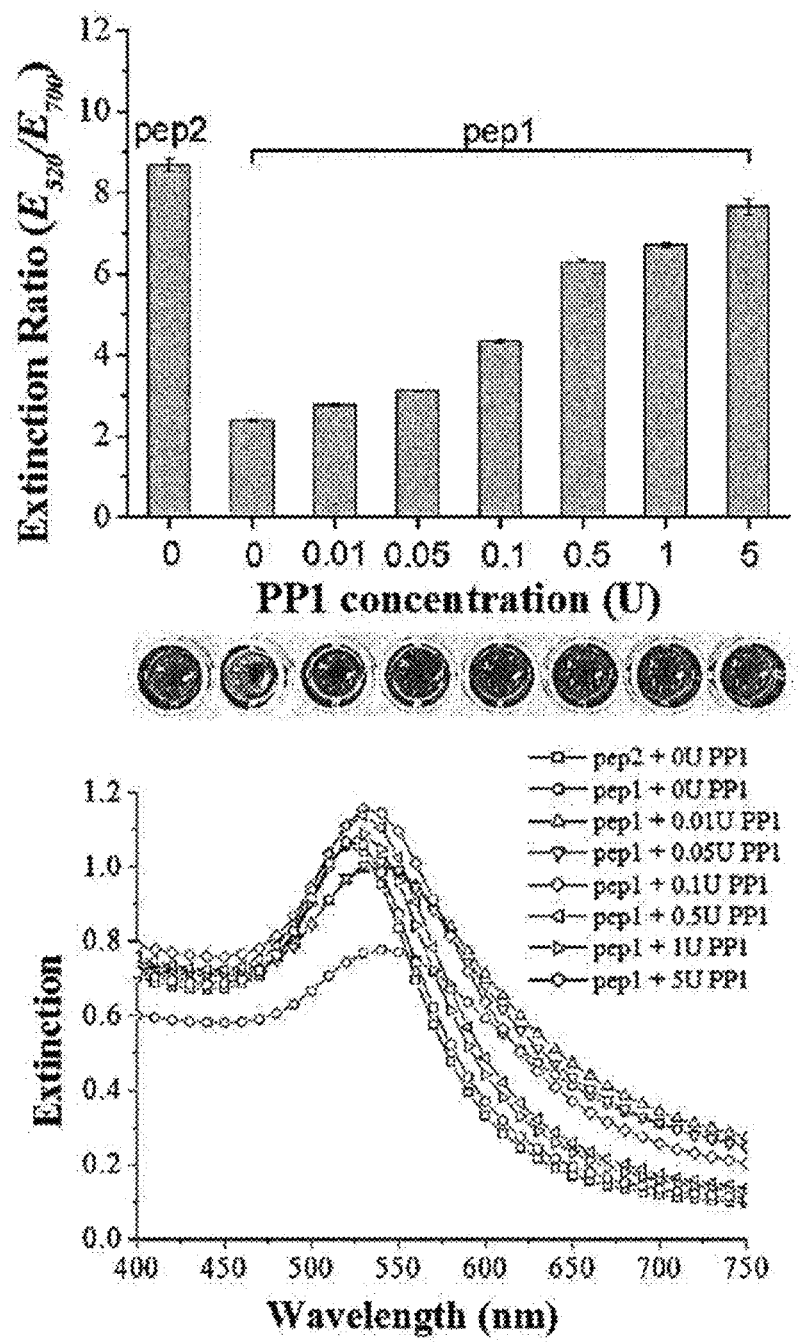
FIG. 10 illustrates analysis results of an absorbance ratio (520 nm/700 nm) of pep1 according to phosphatase concentration.

As a result, it was confirmed that, when pep1 was used, the self-assembled structure of gold nanoparticles was disassembled as the concentration of PP1 increased (see FIG. 10).

Example 9: Colorimetric Assay Using Gold Nanoparticles and $Zn^{2+}$ Ions (3)

Figure 11A:
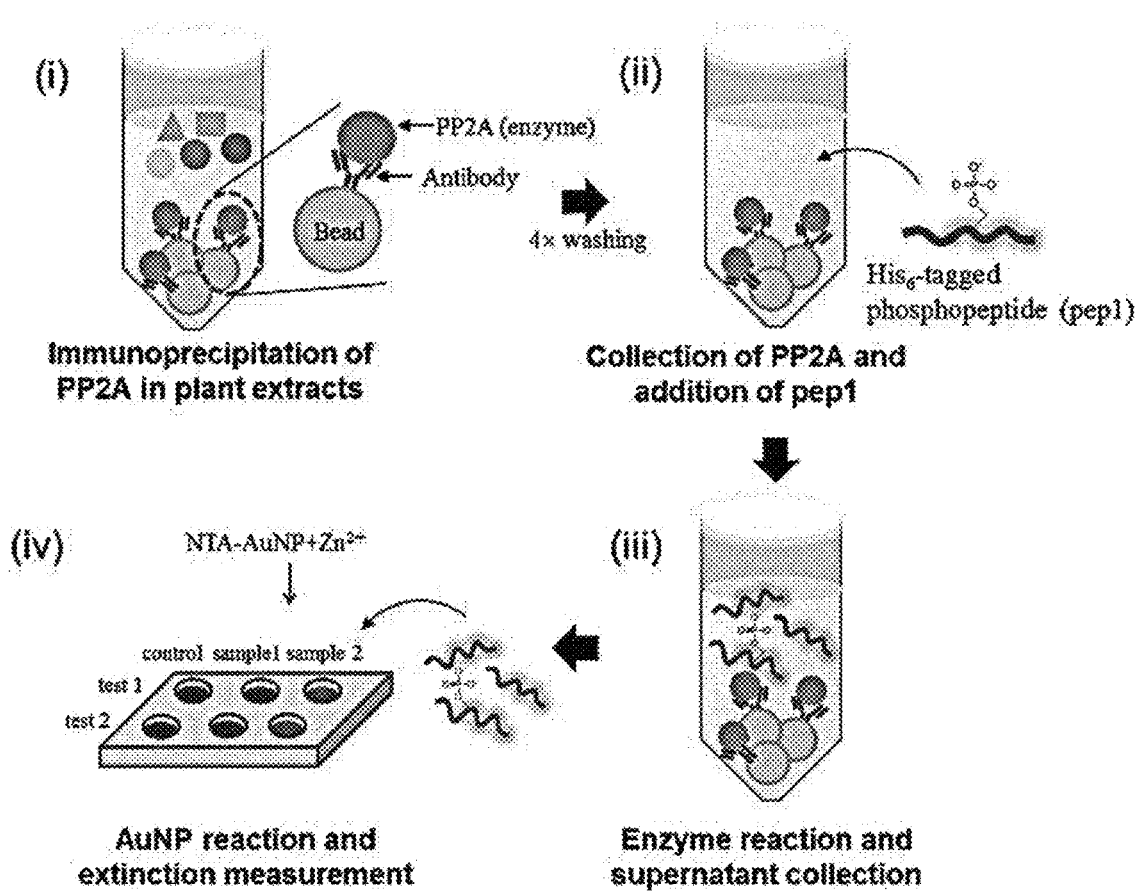
FIG. 11A illustrates an experimental method of agglomeration of gold nanoparticles using plants exhibiting different expression behaviors of PP2A-A1.

Protein A agarose beads (100 μl of resin slurry) were divided into 50 μl aliquots, each aliquot was washed with 1 ml of 50 mM Tris buffer, and this process was repeated twice. 4.64 mg/ml of a homemade rabbit polyclonal antibody using 9.28 μg of GFP antigen [EGFP-6His] was added to the beads and bound thereto at 4□ overnight. Wild-type Columbia-0 (Col-0) not expressing PP2A-A1 and a RCN1-type plant, *Arabidopsis thaliana*, overexpressing PP2A-A1 (expressed as PP2A-A1-YFP) were completely frozen using liquid nitrogen, and then suspended in an extraction buffer (50 mM Tris-HCl, pH 7.5, 50 mM NaCl, 0.3 M sucrose, 1% Triton X-100, 1× protease inhibitor cocktail, and 0.2 mM PMSF). The centrifugation was performed thereon at 4000 rpm for 6 minutes, and then the supernatant was filtered by Miracloth, and then spun down again for 10 minutes. The used antibody is capable of strongly binding to YFP as well as EGFP, and thus the supernatant was mixed with the GFP antibody-bound protein-A agarose beads and bound thereto for 1 hour and 15 minutes. After the reaction, the beads were washed four times with a wash buffer ((50 mM Tris-HCl (pH 7.5), 50 mM NaCl, 0.3 M sucrose, 0.2% Triton X-100, 1× protease inhibitor cocktail, and 0.2 mM PMSF). The washed beads were centrifuged again at 1000 rpm for 5 minutes to remove the supernatant, followed by mixing with 42.5 μl of 20 mM Tris buffer, 5 μl of a manganese ion solution (10 mM), and 2.5 μl of peptide (100 μM) and then allowed to react at room temperature for 1 hour. The supernatant obtained after centrifugation of the reaction product at 1000 rpm for 5 minutes was added to a 96-well plate in which 37.5 μl of 20 mM Tris buffer, 2.5 μl of gold nanoparticles, and 10 μl of a zinc ion solution (10 mM) had been previously mixed, and then allowed to react at room temperature for 1 hour, followed by absorbance measurement (see FIG. 11A).

Figure 11B:
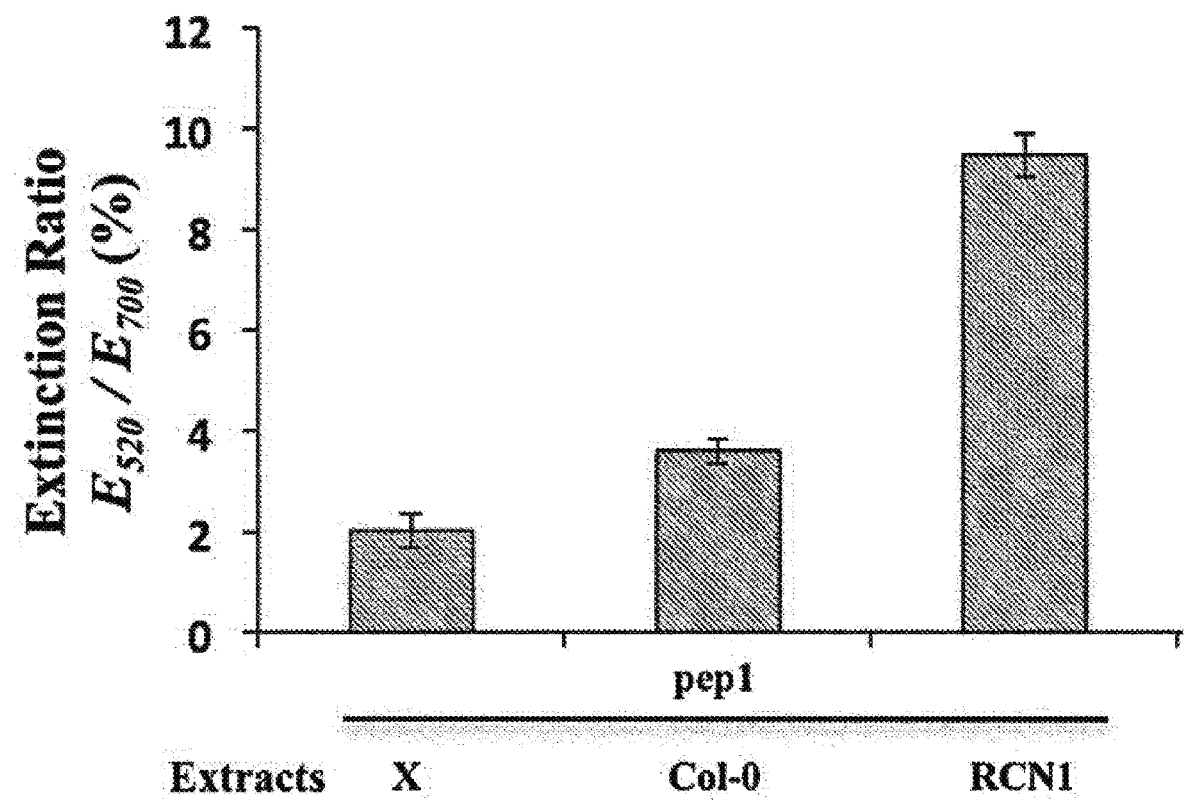
FIG. 11B illustrates experimental results of agglomeration of gold nanoparticles according to the PP2A-A1 expression behavior of plants.

As a result, it was confirmed that the self-assembly of the gold nanoparticles strongly occurred in the case of Col-0 without PP2A-A1, while the self-assembly of the gold nanoparticles was suppressed in an extract of the RCN1-type plant overexpressing PP2A-A1, resulting in a high absorbance ratio (see FIG. 11B).

Figure 12A:
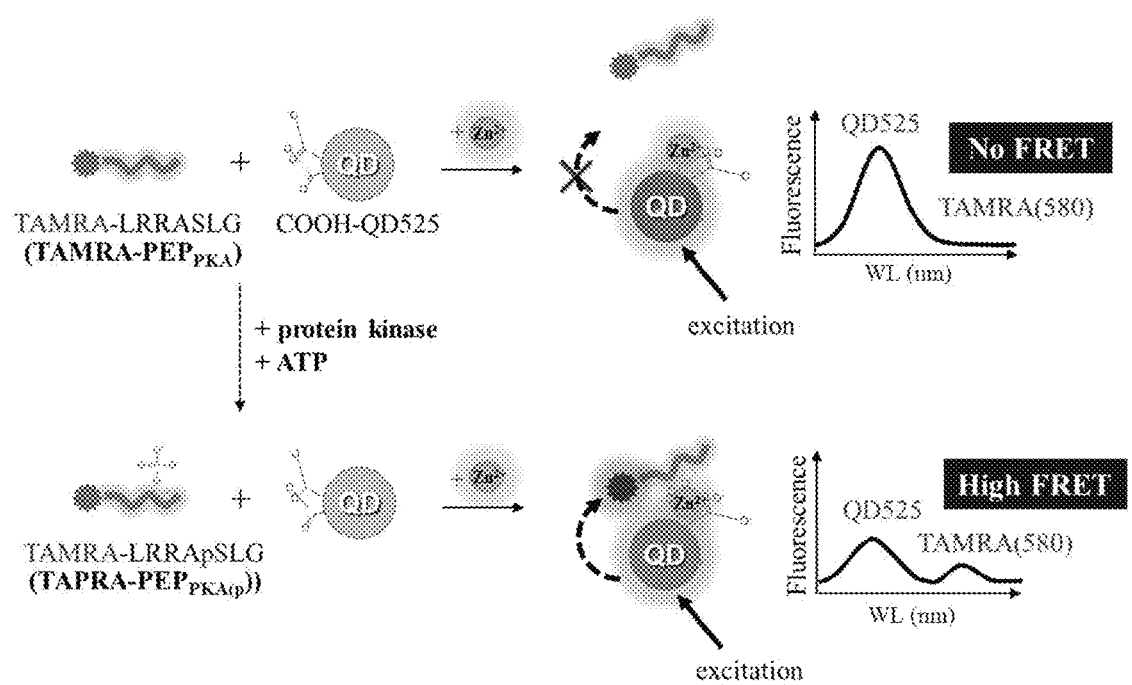
FIG. 12A illustrates a process of FRET test between QDs and TAMRA-PEPPKA or TAMRA-PEPPKA(p).
Figure 12B:
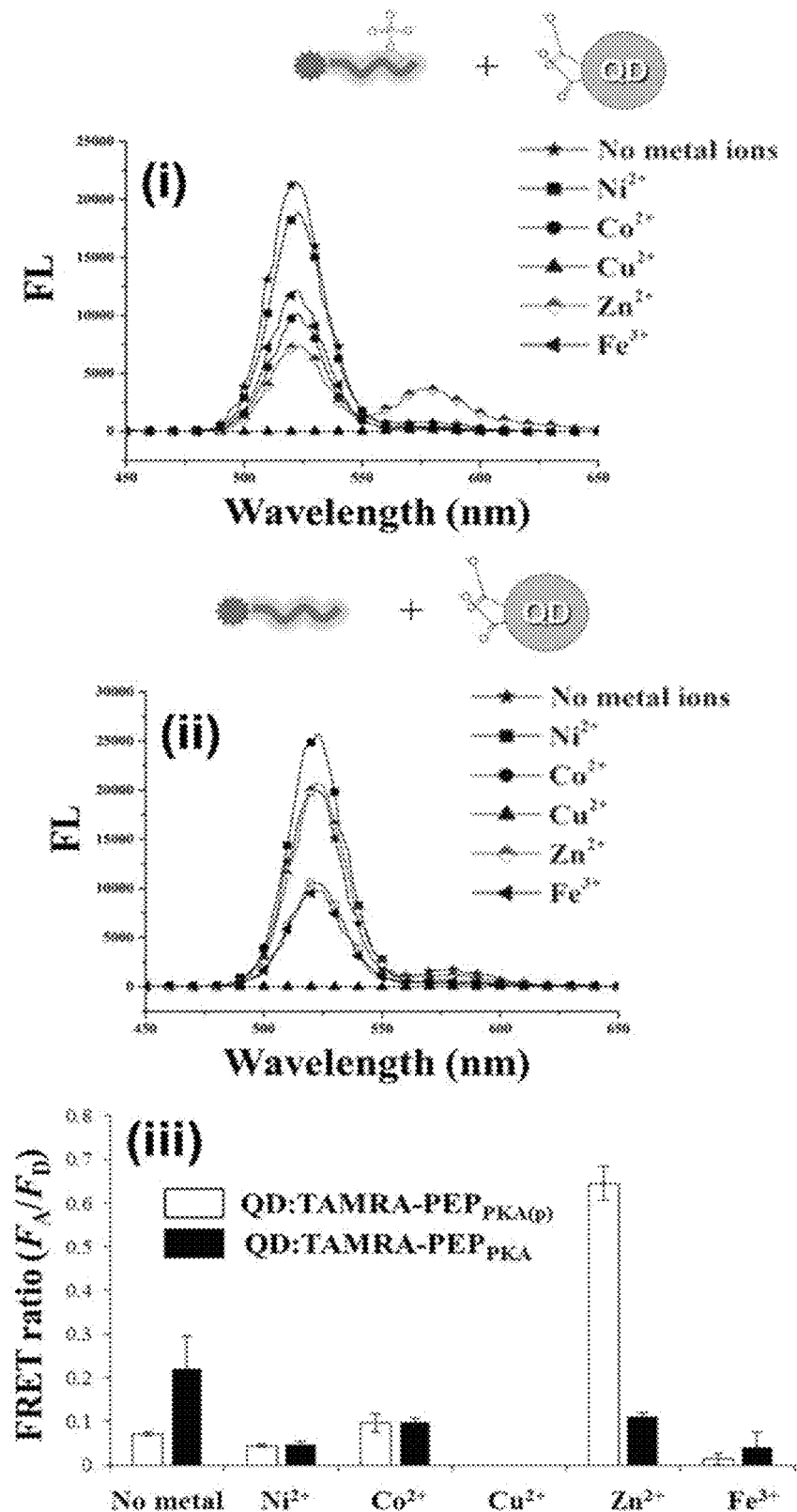
FIG. 12B illustrates measurement results of FRET spectra and FRET ratios (F580/F525) between QDs and TRAMRA-PEPPKA(p) or TAMRA-PEPPKA according to the type of metal ions. Fluorescent spectra of QDs with either (i) TAMRA-LRRApSLG (TAMRA-PEPPKA(p)); or (ii) TAMRA-LRRASLG (TAMRA-PEPPKA) in the presence of different metal ions; (iii) Effect of metal ions on the QD-FRET ratios of TAMRA-PEPPKA(p) (white bar) and TAMRA-PEPPKA (black bar). The FRET ratio was determined by the acceptor (FA) emission area (integrated from 550 to 650 nm) relative to the donor ($F_D$) emission area (integrated from 450 to 550 nm).

Example 10: Test for FRET Signal Detection Between QDs and TAMRA-PEP$_{PKA}$ or TAMRA-PEP$_{PKA(p)}$ A synthetic peptide substrate labeled with 5(6)-carboxytetramethylrhodamine at the N-terminus (TAMRA-LR-RASLG; TAMRA-PEP$_{PKA}$) was compared with its phosphorylated form (TAMRA-LRRApSLG; TAMRA-PEP$_{PKA(p)}$) (FIG. 12B). The FRET ratio was determined by the acceptor ($F_A$) emission area (integrated from 550 to 650 nm) relative to the donor ($F_D$) emission area (integrated from 450 to 550 nm). The concentrations of QD, TAMRA-PEP$_{PKA(p)}$ (or TAMRA-PEP$_{PKA}$), and $ZnCl_2$ were 2 nM, 80 nM and 100 μM, respectively. The QD-FRET spectra were obtained at an excitation wavelength of 380 nm.

Figure 1:
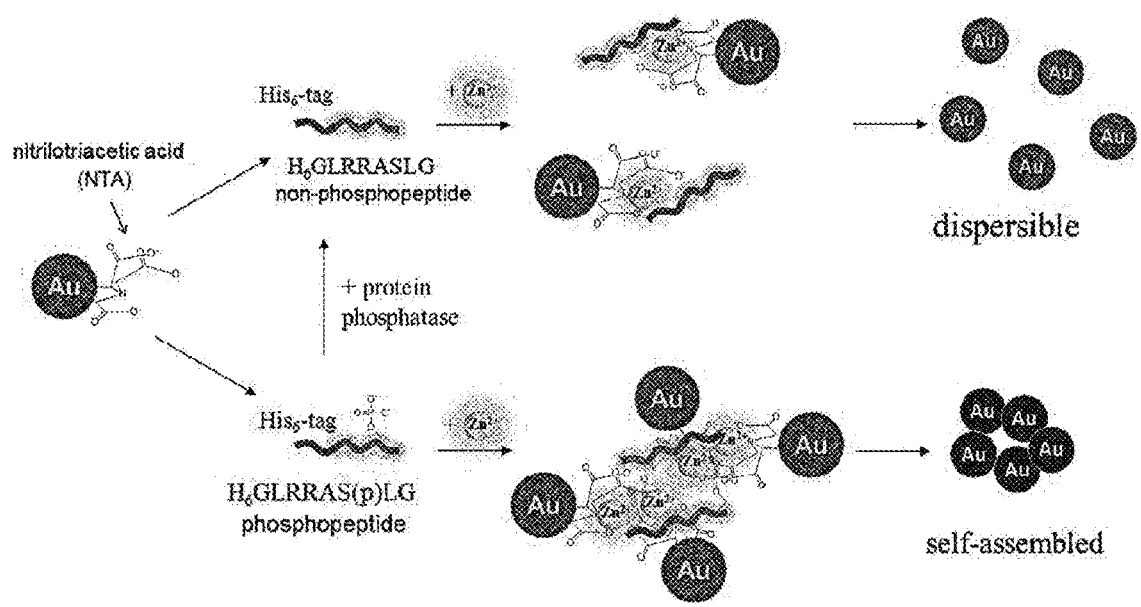
FIG. 1 is a view illustrating a method of measuring kinase or phosphatase activity using the self-assembly of metal nanoparticles.
Figure 2:
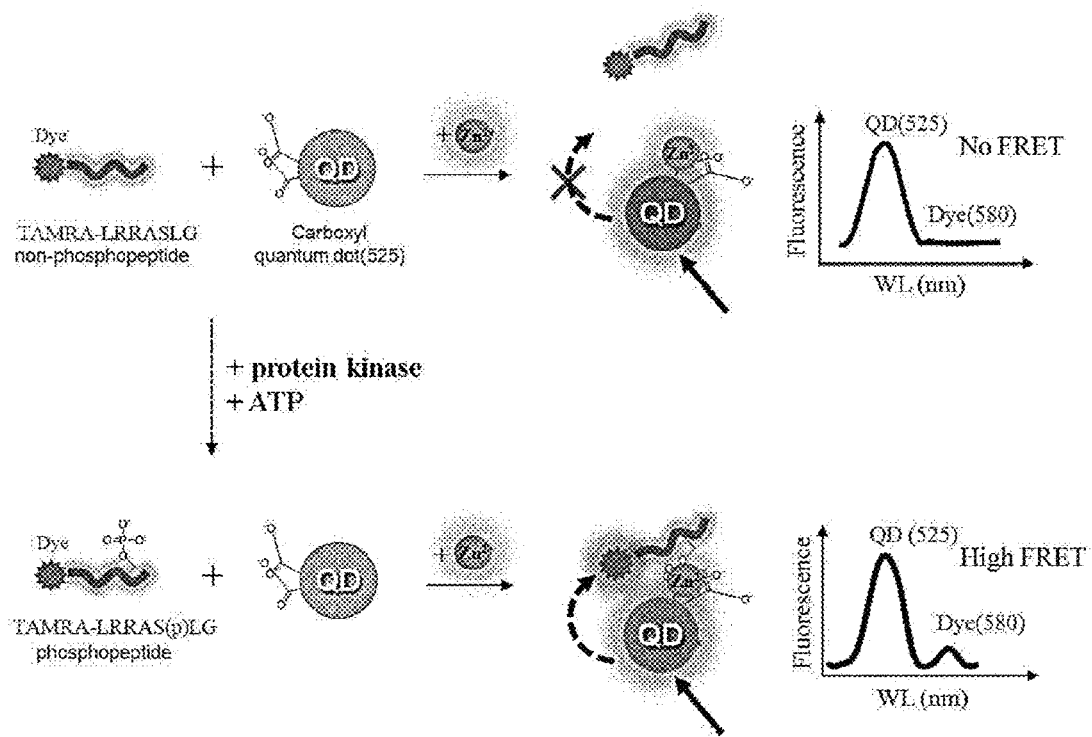
FIG. 2 illustrates a method of measuring kinase or phosphatase activity using an FRET signal.

While divalent metal ions (Ni(II), Co(II), Cu(II), and Zn(II)) and a trivalent metal ion (Fe(III)) were tested, only Zn(II) ion triggered a strong association between the energy donor and acceptor of the QD-FRET in the presence of TAMRA-PEP$_{PKA(p)}$ (FIG. 12B (i) and (ii)). Since $Cu^{2+}$ completely quenched the fluorescence intensity of QDs, there were no signals in QD-FRET at both acceptors. This Zn(II)-coordination led to a high FRET ratio ($F_A/F_D$, 0.65), which is defined by the acceptor ($F_A$) integrated emission relative to donor ($F_D$) integrated emission (FIG. 1C), whereas other metal ions did not produce a significant FRET ratio. In addition, non-phosphopeptides resulted in a marginal FRET ratio even in the presence of Zn(II). This result strongly indicates that Zn(II) is specifically associated with phosphopeptides on the surfaces of QDs. In the present study, the FRET ratio was saturated at a 1:40 molar ratio of QD to T-pPEP1 in the presence of Zn(II) ion when the concentration of QD was fixed to 2 nM.

Example 11: Test for FRET Signal Detection According to a Concentration of Metal Ions The change in FRET between QD and TAMRA-PEPPKA (p) according to a function of $Zn^{2+}$ concentration was calculated. Furthermore, the relative FRET percentage was calculated by dividing the experimental FRET ratio by the maximal FRET ratio (0.74). The concentrations of QD and TAMRA-PEP$_{PKA(p)}$ were 2 nM and 80 nM, respectively. Excitation/emission wavelengths of QD-FRET (FIG. 12C (i)), QD (FIG. 12C (ii)), and TAMRA-PEP$_{PKA(p)}$ (FIG. 12C (iii)) were obtained at 380/580, 380/525, 530/580 nm, respectively.

Figure 12C:
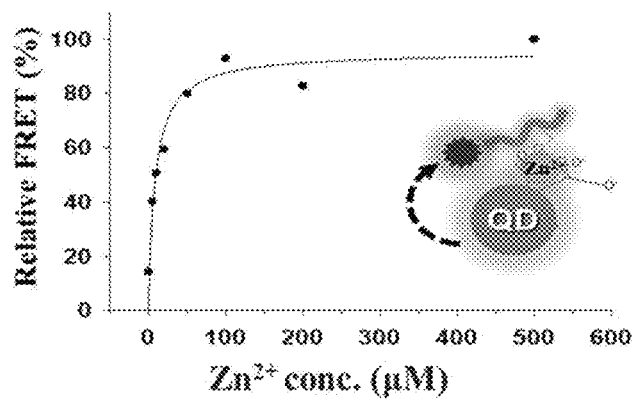
FIG. 12C illustrates a change of FRET ratios between QDs and TRAMRA-PEPPKA(p) according to a concentration of Zn2+ ions (i); a change of fluorescence intensities between QD and fluorescence peptide according to a concentration of metal ions. Changes in FRET (i) between QD and TAMRA-PEPPKA(p) as a function of Zn2+ concentration. The relative FRET percentage was calculated by dividing the experimental FRET ratio by the maximal FRET ratio (0.74). Fluorescence intensities of donor (QD); (ii) and acceptor (TAMRA-PEPPKA(p)); (iii) as a function of metal ion (Zn2+, Ni2+, Co2+, and Fe3+) concentration.
Figure 12C:
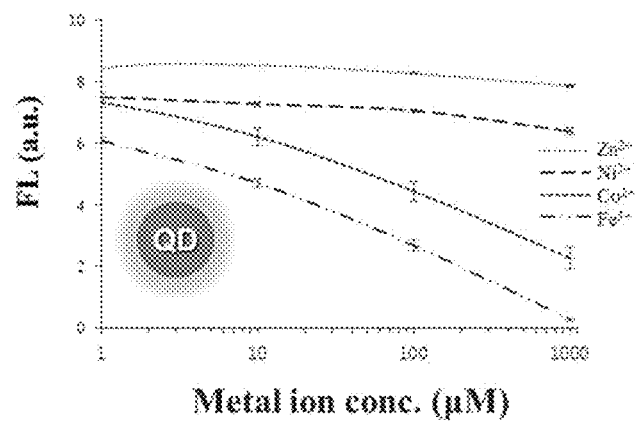
Figure 12C:
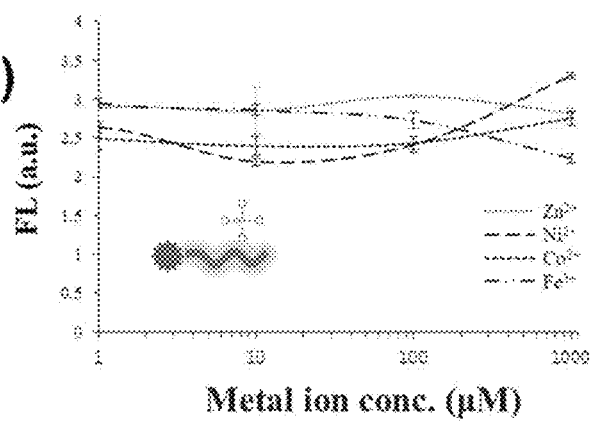

The FRET ratio was also dependent on Zn(II) concentration, where maximum FRET ratio was acquired over the range of >100 µM Zn(II) at a 1:40 molar ratio of QD to TAMRA-PEP$_{PKA(p)}$ (FIG. 12C (i)). Considering the hydrodynamic diameter (10-20 nm) and multivalent capacity of carboxyl QD525, 40 times more fluorescent peptides were not fully saturated relative to QDs, but this number was optimized between QD/TAMRA-PEP$_{PKA(p)}$ and QD/TAMRA-PEP$_{PKA}$ in terms of signal-to-background ratio. Compared to Zn(II)-caged complexes capable of capturing the phenyl phosphate dianion, free Zn(II) ions in this study revealed a relatively low binding affinity of $K_d$=8.8 µM for TAMRA-PEP$_{PKA(p)}$, based on the FRET efficiency. When we examined the effect of metal ions (except but $Cu^{2+}$) on the florescence intensity of donor QD or acceptor dye, $Zn^{2+}$ and $Ni^{2+}$ ions did not affect the emission intensities of QD and TAMRA-PEP$_{PKA(p)}$ (FIG. 12C (ii) and (iii)), whereas $Co^{2+}$ and $Fe^{3+}$ reduced the emission intensity of QD as their concentrations increased (FIG. 12C (ii)). As a consequence, since free Zn(II) ions even at high concentration did not influence fluorescent intensity of the donor QD or the acceptor TAMRA-PEP$_{PKA(p)}$, they are favorable for use in the FRET-based method in order to avoid synthesis of complex chemicals, which may adversely affect the fluorophores. Therefore, this result suggests that our Zn(II)-mediated QD-FRET would be useful for detecting phosphopeptides without complex metal-chelating ligands.

Example 12: Test for FRET Signal Detection

Time-dependent change in the QD-FRET ratio in the presence (black diamond) and absence (black square) of Zn(II) (i); and peptide phosphorylation-dependent change in the QD-FRET ratio (ii) were confirmed. Total concentration of peptides (TAMRA-PEP$_{PKA(p)}$ and TAMRA-PEP$_{PKA}$) was kept constant at 80 nM, while TAMRA-PEP$_{PKA(p)}$ concentration was varied (0, 25, 75, and 100%). The concentrations of QD and metal ions were 2 nM and 100 µM, respectively. The QD-FRET spectra were obtained at an excitation wavelength of 380 nm.

Figure 12D:
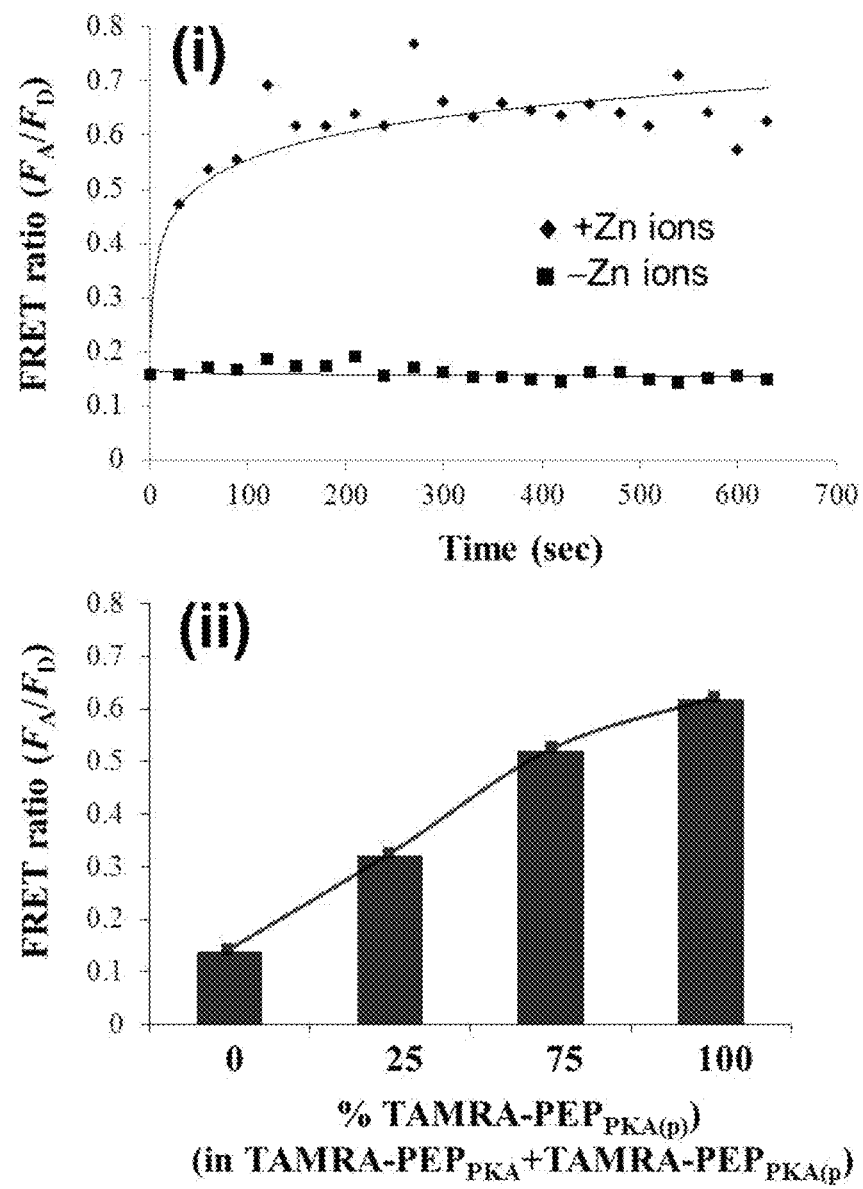
FIG. 12D illustrates a change of FRET ratio between QD and TAMRA-PEPPKA(p) according to time (i), and a change of FRET of QD according to a ratio of TAMRA-PEPPKA and FRET TAMRA-PEPPKA(p). Time-dependent change in the QD-FRET ratio in the presence (black diamond) and absence (black square) of Zn(II) (i); and peptide phosphorylation-dependent change in the QD-FRET ratio (ii).

To examine kinetics and phosphorylation-dependency of this FRET phenomenon, we examined time-dependent FRET ratio in the presence and absence of Zn(II) ion (FIG. 12D (i)), and compared the FRET ratios at varied proportions of phosphorylated peptide (FIG. 12D (ii)). The maximum FRET ratio was reached within 5 min after addition of Zn(II) ion, whereas no addition of Zn(II) did not change the FRET ratio. Under the same conditions, where the molar ratio of QD to peptide was 1:40 in the presence of Zn(II), the FRET ratio was proportional to the TAMRA-PEP$_{PKA(p)}$ concentration Example 13: Test for FRET Signal Detection according to Phosphorylated State of Peptide Substrate 71 µl of 20 mM Tris-HCl buffer (pH 7.4), 20 µl of 20 nM Qdot 525 (Invitrogen), and either (8 µl at 1 µM) of TAMRA-PEP$_{HSF-1}$ (TAMRA-KEEPPSPPQSPR), TAMRA-PEP$_{HSF-1(P)}$ (TAMRA-KEEPPSPPQpSPR), or TAMRA-PEP$_{HSF-1(PP)}$ (TAMRA-KEEPPpSPPQpSPR) were mixed and transferred to a 96-well plate. 1 µl of a 10 mM zinc ion solution were further added to the 96-well plate, and then the aforementioned materials were satisfactorily mixed together in this order and allowed to react at room temperature for about 5 minutes, followed by measurement of a fluorescence signal using a plate reader.

Figure 13A:
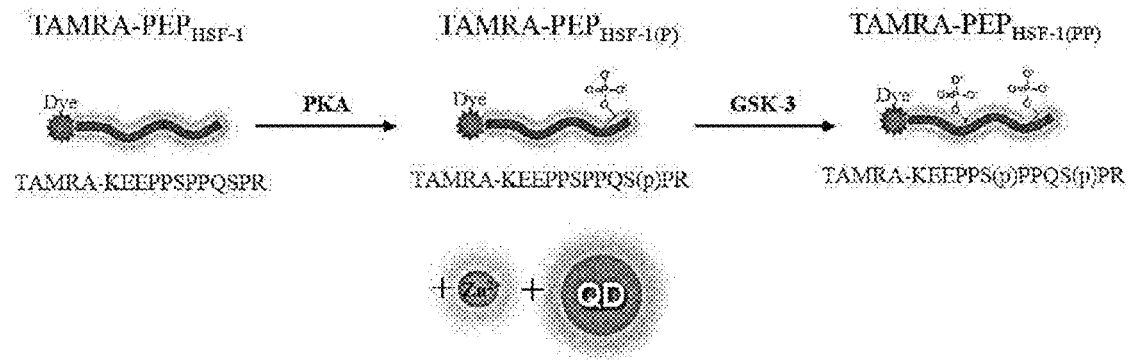
FIG. 13A illustrates a process of phosphorylating TAMRA-$PEP_{HSF-1}$.

The initially synthesized TAMRA-PEP$_{HSF}$-1 is a substrate in which a phosphor is bound to a peptide derived from Heat shock factor-1 (HSF-1), which is a substrate protein, and the substrate is consecutively phosphorylated by mitogen-activated protein kinase (MAPK) and glycogen synthase kinase-3 (GSK-3). Serine at the C-terminal of the peptide sequence is first phosphorylated by protein kinase A (PKA), and the phosphorylated serine at the C-terminal is recognized by GSK-3 to phosphorylate serine at the N-terminal (see FIG. 13A).

As the 96-well plate, a FluoroNunc 96-well plate available from Nunc was used, an excitation wavelength was 380 nm, and a measurement wavelength was in the range of 450 nm to 650 nm. A measurement time for each wavelength was 0.8 ms.

Figure 13B:
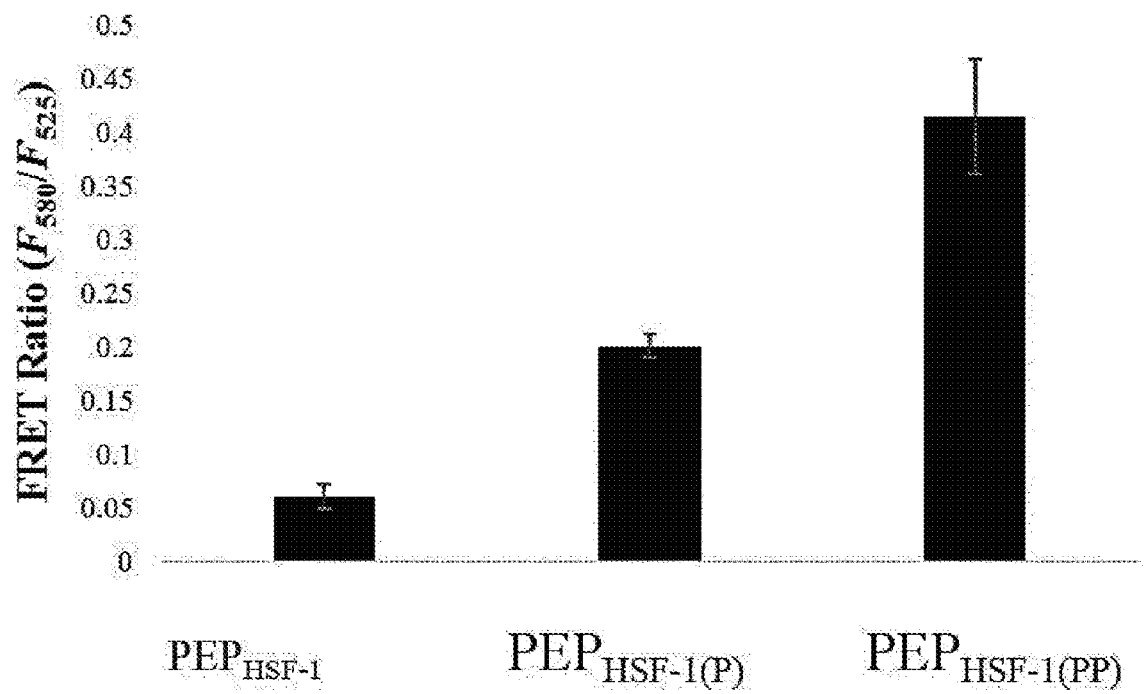
FIG. 13B illustrates measurement results of an FRET ratio ($F_{580}/F_{525}$) according to the phosphorylated state of $PEP_{HSF-1}$.

As a result, as illustrated in FIG. 13B, a higher FRET ratio ($F_{580}/F_{525}$) was detected as consecutive phosphorylation proceeded.

Example 14: Test for FRET Signal Detection Using NeutrAvidin Agarose Beads

Figure 14A:
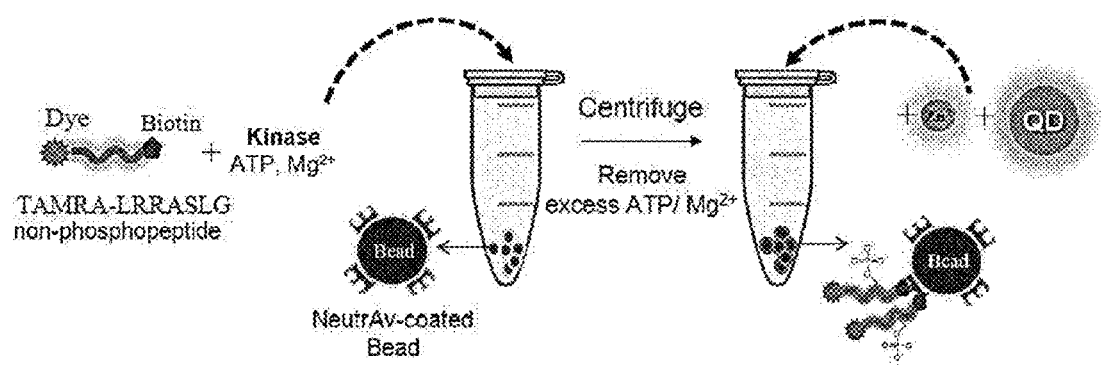
FIG. 14A illustrates a test method of detecting an FRET signal using NeutrAvidin agarose beads in Example 11.
Figure 14B:
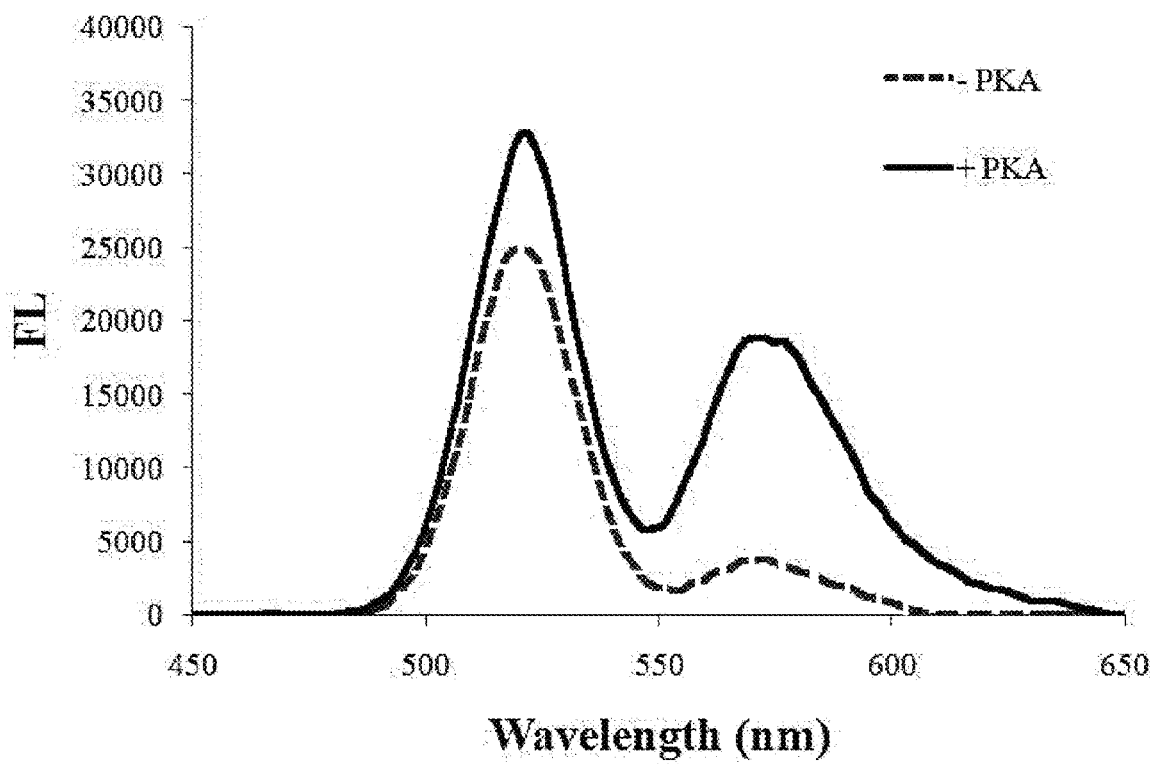
FIGS. 14B and 14C illustrate test results of FRET signal detection using NeutrAvidin agarose beads.

Unlike Example 13, to implement a method of effectively removing a substance that affects an FRET signal (salt, metal ions, ATP, DTT, or the like), biotin was bound to one end of a peptide substrate to induce a kinase reaction, and then the substrate having undergone the kinase reaction through NeutrAvidin-biotin binding was effectively isolated, followed by FRET signal detection (see FIG. 14A). TAMRA-PEP$_{PKA}$(TAMRA-LRRASLG) was used as an initial peptide substrate, the substrate is a substrate in which a phosphor was bound to a peptide derived from protein Porcine liver pyruvate kinase, and the substrate was phosphorylated by PKA. TAMRA-PEP$_{PKA}$-Biotin(biotin-LRRASLG-TAMRA), which is a substrate to which biotin is further bound to the peptide substrate, was synthesized and finally applied to the experiment. In particular, 78 µl of 20 mM Tris-HCl buffer (pH 7.4), 5 µl of 100 µM TAMRA-PEP$_{PKA}$-biotin, 10 µl of a PKA reaction buffer (10×), 2 µl of a 10 mM ATP solution, and 5 µl of a 25 U PKA enzyme were sequentially mixed in a 1.5 ml tube, and then allowed to react at 30□ for 1 hour and 30 minutes. At this time, a control not including a PKA enzyme in the 1.5 ml tube was used to conduct a comparative experiment. Thereafter, 50 µl of 50% NeutrAvidin agarose bead slurry were added thereto, and mixed by vortexing for 30 minutes, followed by centrifugation at 1500 rpm for 5 minutes to remove the supernatant therefrom. Afterwards, 50 µl of TAMRA-PEP$_{PKA}$-Biotin-tagged NeutrAvidin bead slurry was added to a 96-well plate, 80 µl of 20 mM Tris-HCl buffer (pH 7.4), 20 µl of 20 nM Qdot 525, and 1 µl of a 10 mM zinc ion solution were sequentially added thereto and mixed well, and then the mixture was allowed to react at room temperature for about 5 minutes, followed by measurement of a fluorescence signal using a plate reader.

Figure 14C:
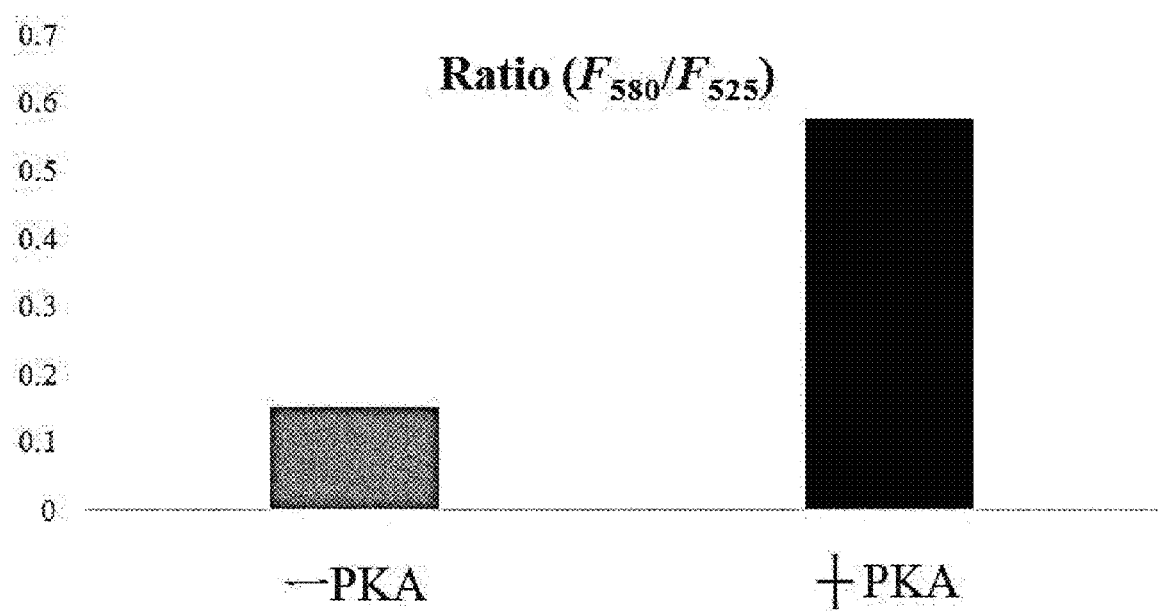
Figure 15:
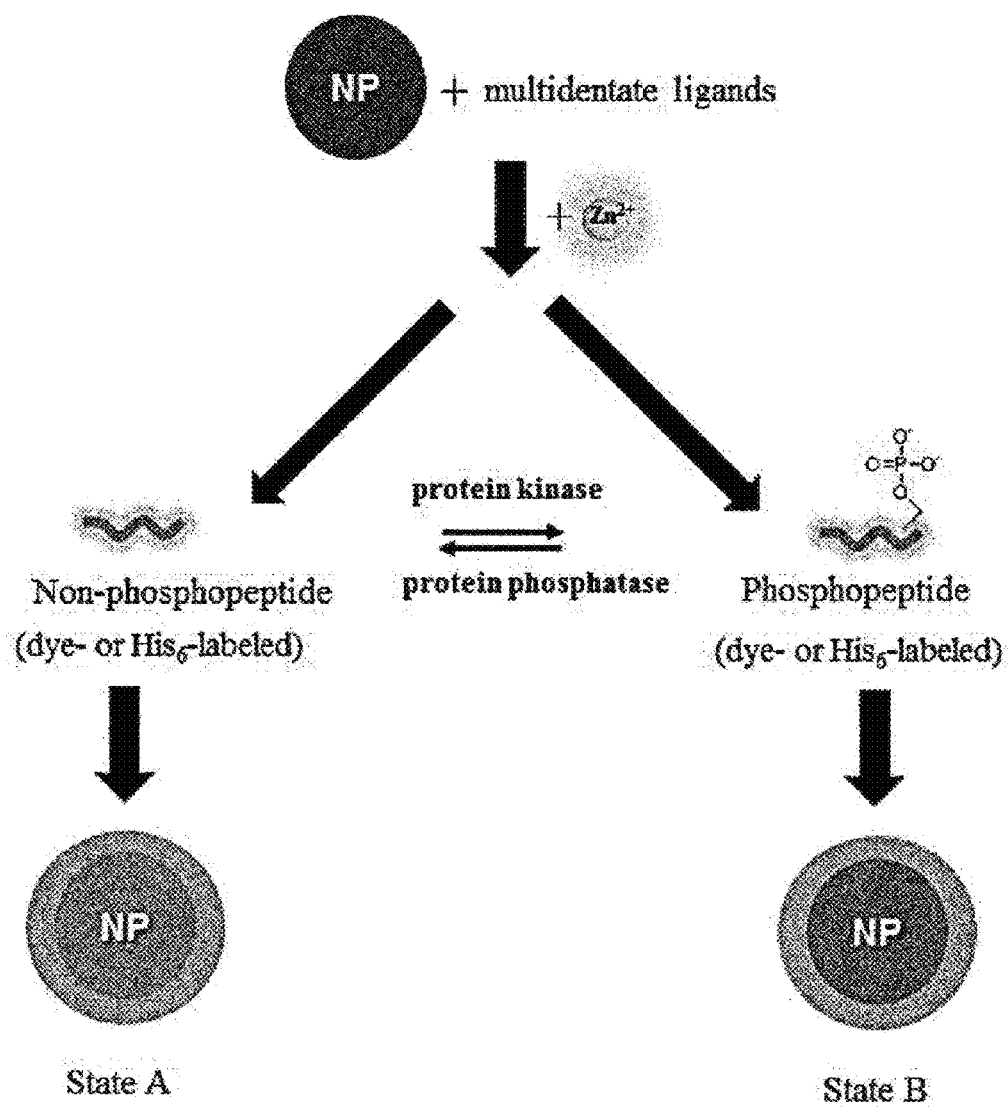
FIG. 15 is a conceptual view illustrating phosphopeptide detection using nanoparticles and $Zn^{2+}$.

As the 96-well plate, a FluoroNunc 96-well plate available from Nunc was used, an excitation wavelength was 380 nm, and a measurement wavelength was in the range of 450 nm to 650 nm. A measurement time for each wavelength was 0.8 ms. The bar graph in FIG. 14C shows calculation results of a ratio of two highest peaks of the measured fluorescence spectrum, which indicates a calculated value obtained by dividing a fluorescence value at 580 nm by a fluorescence value at 525 nm.

As a result, it was confirmed that the FRET ratio was about 0.16 when the PKA enzyme was absent, while a signal value of 0.59 was observed as the FRET ratio in the tube including the PKA enzyme, which means that PKA enzymatic activity can be effectively detected even in the presence of an inhibitor in a reaction buffer.

While present invention has been described in detail with reference to exemplary embodiments thereof, it is obvious to those of ordinary skill in the art that these embodiments are provided only for illustrative purposes, and are not intended to limit the scope of the present invention. Thus, the substantial scope of the present invention should be defined by the appended claims and equivalents thereto.

Characteristics and advantages of the present invention are summarized as follows:

(a) The present invention provides a composition for measuring kinase or phosphatase activity.

(b) The present invention provides a method of measuring phosphatase activity and a method of measuring kinase activity.

(c) The present invention provides a method of screening a phosphatase activity inhibitor.

(d) When the composition and methods of the present invention are used, the kinase or phosphatase activity may be quantitatively detected in real time.

(e) When the composition and methods of the present invention are used, a material capable of inhibiting phosphatase activity may be discovered.

What is claimed is:

1. A composition for measuring kinase or phosphatase activity comprising
   (a) zinc ions ($Zn^{2+}$),
   (b) a zinc ion receptor comprising a chelating ligand, and
   (c) a kinase or phosphatase peptide substrate, comprising a fluorescence signal-generating donor fluorophore,
      wherein the zinc ion receptor comprises a fluorophore acceptor that quenches a fluorescence signal by causing fluorescence resonance energy transfer (FRET) with the donor fluorophore, and exhibiting a phosphorylation or dephosphorylation detection signal according to a change in a phosphorylation state of the peptide substrate.

2. The composition of claim 1, wherein the peptide substrate is immobilized on a support.

3. The composition of claim 2, wherein the peptide substrate further comprises biotin, and the support is deglycosylated avidin agarose beads.

4. A method of measuring phosphatase activity, the method comprising the following processes:
   (i) preparing a composition for measuring phosphatase activity, wherein the composition comprises (a) zinc ions, (b) a fluorophore acceptor as a zinc ion receptor comprising a chelating ligand, and (c) a phosphorylated phosphatase peptide substrate to which a donor fluorophore is bound, and a fluorescence signal of the donor fluorophore is quenched by an interaction between the zinc ions and the fluorophore acceptor; and
   (ii) detecting recovery of the fluorescence signal having been quenched by FRET by contacting the composition with a phosphatase.

5. A method of measuring kinase activity, the method comprising the following processes:
   (i) preparing a composition for measuring kinase activity, wherein the composition comprises (a) zinc ions, (b) a fluorophore acceptor as a zinc ion receptor comprising a chelating ligand, and (c) a kinase peptide substrate to which a donor fluorophore is bound, and the kinase peptide substrate comprises one or more dephosphorylated phosphorylation site peptides; and
   (ii) detecting quenching of a fluorescence signal by FRET by contacting the composition with a kinase.

* * * * *